(12) United States Patent
Pryor et al.

(10) Patent No.: US 11,750,944 B2
(45) Date of Patent: Sep. 5, 2023

(54) PIXEL NOISE CANCELLATION SYSTEM

(71) Applicant: Varex Imaging Corporation, Salt Lake City, UT (US)

(72) Inventors: Paul Pryor, West Jordan, UT (US); Pieter G. Roos, Sandy, UT (US); Richard Weisfield, Los Altos, CA (US)

(73) Assignee: Varex Imaging Corporation, Salt Lake City, UT (US)

( * ) Notice: Subject to any disclaimer, the term of this patent is extended or adjusted under 35 U.S.C. 154(b) by 164 days.

(21) Appl. No.: 17/334,353

(22) Filed: May 28, 2021

(65) Prior Publication Data

US 2022/0385837 A1 Dec. 1, 2022

(51) Int. Cl.
*H04N 25/616* (2023.01)
*H04N 5/32* (2023.01)
(Continued)

(52) U.S. Cl.
CPC ............ *H04N 25/616* (2023.01); *H04N 5/32* (2013.01); *H04N 23/30* (2023.01); *H04N 25/30* (2023.01); *H04N 25/60* (2023.01); *H04N 25/65* (2023.01); *H04N 25/677* (2023.01); *H04N 25/70* (2023.01); *H04N 25/701* (2023.01); *H04N 25/75* (2023.01); *H04N 25/766* (2023.01); *A61B 6/00* (2013.01); *A61B 6/02* (2013.01); *A61B 6/027* (2013.01); *A61B 6/4021* (2013.01); *H04N 25/78* (2023.01)

(58) Field of Classification Search
CPC ...... H04N 25/30; H04N 25/60; H04N 25/616; H04N 25/65; H04N 25/677; H04N 25/32; H04N 25/766
See application file for complete search history.

(56) References Cited

U.S. PATENT DOCUMENTS 6,538,591 B2  3/2003  Sato et al.
7,796,174 B1  9/2010  Harwit et al.
(Continued)

FOREIGN PATENT DOCUMENTS

EP   2806628 A1 * 11/2014 ............... H04N 5/32
WO   9907138    2/1999

OTHER PUBLICATIONS

Fowler et al., Reset Noise Reduction in Capacitive Sensors, IEEE Transactions on Circuits and Systems, vol. 53, No. 3, Aug. 2006.
(Continued)

*Primary Examiner* — David N Werner
(74) *Attorney, Agent, or Firm* — Laurence & Phillips IP Law

(57) ABSTRACT

Some embodiments include a system, comprising: a plurality of pixels; a plurality of data lines coupled to the pixels; a plurality of switches coupling the pixels to the data lines; a plurality of readout circuits coupled to the data lines; control logic coupled to the readout circuits, the control logic configured to, for one of the pixels: acquire a first value for the pixel while the corresponding switch is in an off state; reset the corresponding readout circuit corresponding for the pixel; acquire a second value for the pixel after resetting the readout circuit; turn on the corresponding switch; acquire a third value for the pixel after turning on the corresponding switch; and combine the first value, the second value, and the third value into a combined value for the pixel.

20 Claims, 22 Drawing Sheets

(51) Int. Cl.

| | |
|---|---|
| *H04N 25/75* | (2023.01) |
| *H04N 25/30* | (2023.01) |
| *H04N 25/60* | (2023.01) |
| *H04N 25/766* | (2023.01) |
| *H04N 25/65* | (2023.01) |
| *H04N 25/677* | (2023.01) |
| *H04N 23/30* | (2023.01) |
| *H04N 25/70* | (2023.01) |
| *H04N 25/701* | (2023.01) |
| *A61B 6/00* | (2006.01) |
| *A61B 6/02* | (2006.01) |
| *H04N 25/78* | (2023.01) |

(56) References Cited

U.S. PATENT DOCUMENTS

| | | | |
|---|---|---|---|
| RE41,865 E | 10/2010 | Choi | |
| 8,558,929 B2 | 10/2013 | Tredwell | |
| 9,332,950 B2 | 5/2016 | Spartiotis et al. | |
| 9,478,692 B1 | 10/2016 | Twede et al. | |
| 10,498,989 B1 | 12/2019 | Oh et al. | |
| 2001/0002045 A1* | 5/2001 | Fossum | H04N 25/75 |
| | | | 348/E3.018 |
| 2001/0012070 A1 | 8/2001 | Enod et al. | |
| 2003/0085402 A1* | 5/2003 | Tay | H04N 1/32475 |
| | | | 348/E9.037 |
| 2003/0160238 A1* | 8/2003 | Fossum | H01L 27/14627 |
| | | | 348/E3.018 |
| 2003/0169847 A1 | 9/2003 | Karellas et al. | |
| 2005/0035273 A1* | 2/2005 | Machida | H04N 25/616 |
| | | | 250/214.1 |
| 2008/0149843 A1* | 6/2008 | Tredwell | H04N 3/155 |
| | | | 348/E3.018 |
| 2009/0153716 A1* | 6/2009 | Ota | H04N 25/76 |
| | | | 348/241 |
| 2010/0141804 A1 | 6/2010 | Morel et al. | |
| 2011/0058082 A1* | 3/2011 | Tay | H04N 25/65 |
| | | | 348/308 |
| 2011/0228144 A1* | 9/2011 | Tian | H04N 25/709 |
| | | | 348/E9.037 |
| 2012/0138808 A1 | 6/2012 | Jung | |
| 2014/0016879 A1 | 1/2014 | Högasten et al. | |
| 2014/0022427 A1* | 1/2014 | Goto | H04N 23/741 |
| | | | 348/308 |
| 2014/0340552 A1 | 11/2014 | Wuen et al. | |
| 2015/0049230 A1 | 2/2015 | Lee et al. | |
| 2015/0303232 A1* | 10/2015 | Yamazaki | H01L 27/14623 |
| | | | 257/435 |
| 2015/0319382 A1 | 11/2015 | Kawanabe et al. | |
| 2016/0006969 A1* | 1/2016 | Matsumoto | H01L 27/14645 |
| | | | 348/308 |
| 2016/0014361 A1* | 1/2016 | Boukhayma | H04N 25/60 |
| | | | 348/308 |
| 2016/0165164 A1* | 6/2016 | Harada | H04N 25/134 |
| | | | 348/250 |
| 2016/0273961 A1 | 9/2016 | Kim | |
| 2016/0316161 A1* | 10/2016 | Sekine | H04N 25/709 |
| 2017/0019618 A1* | 1/2017 | Koga | H01L 27/14636 |
| 2017/0188987 A1 | 7/2017 | Liu et al. | |
| 2017/0223291 A1* | 8/2017 | Ayers | H04N 23/667 |
| 2018/0054574 A1* | 2/2018 | Park | H04N 23/81 |
| 2018/0109745 A1* | 4/2018 | Maruyama | G06T 5/002 |
| 2018/0269242 A1* | 9/2018 | Kawahito | H04N 25/63 |
| 2019/0082135 A1* | 3/2019 | Furuta | H04N 25/70 |
| 2019/0222783 A1* | 7/2019 | Nishihara | H04N 25/70 |
| 2021/0126025 A1 | 4/2021 | Kennedy et al. | |
| 2021/0327946 A1 | 10/2021 | Guo et al. | |

OTHER PUBLICATIONS

Int'l Appl. No. PCT/US2022/031465, International Search Report dated Sep. 14, 2022.
Int'l Appl. No. PCT/US2022/031465, Written Opinion dated Sep. 14, 2022.
Steven Freestone, Richard Weisfield, Carlo Tognina, Isaias Job, and Richard E. Colbeth, Analysis of a New Indium Gallium Zinc Oxide (IGZO) Detector, Proc. SPIE 11312, Medical Imaging 2020: Physics of Medical Imaging, 113123W (Mar. 16, 2020).
Int'l Appl. No. PCT/US2022/043910, International Search Report dated Jan. 3, 2023.
Int'l Appl. No. PCT/US2022/043910, Written Opinion dated Jan. 3, 2023.
U.S. Appl. No. 17/334,681, Response to Office Action dated Apr. 28, 2023.
U.S. Appl. No. 17/334,681, Office Action dated Nov. 28, 2022.

\* cited by examiner

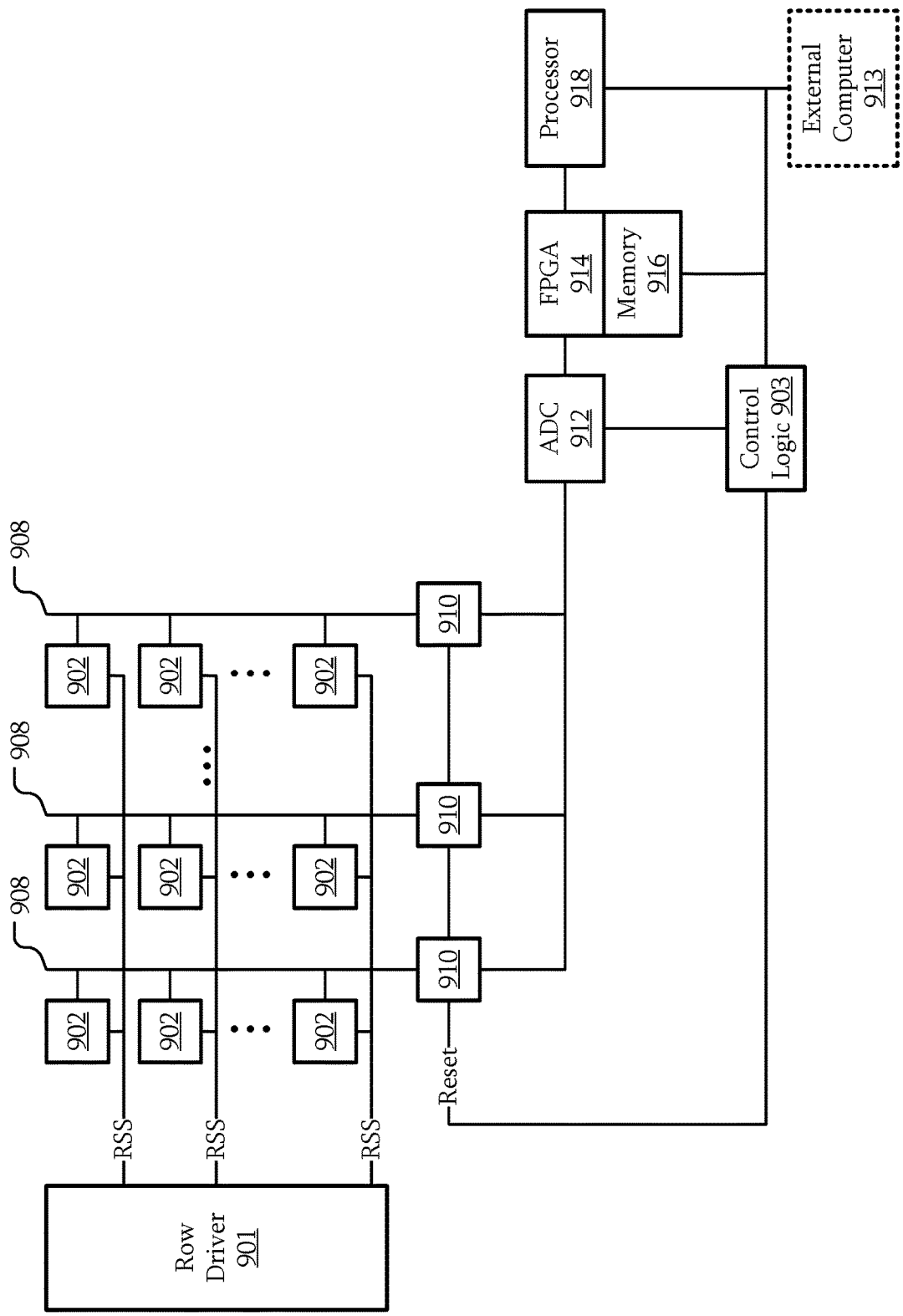

PIXEL NOISE CANCELLATION SYSTEM

X-ray imaging arrays may be used to generate two-dimensional images or video in response to incident x-rays. An imaging strip may be panned around an axis to generate a panoramic image.

Noise may accumulate in a pixel of an imaging array. While various techniques such as correlated double sampling may reduce or eliminate noise due to other components in the chain from the pixel to an image, the noise in the pixel itself may remain.

BRIEF DESCRIPTION OF SEVERAL VIEWS OF THE DRAWINGS

FIG. 9B is a block diagram of an imaging array and associated electronics in the imaging system according to some embodiments.

DETAILED DESCRIPTION

Some embodiments relate to imaging systems including an imaging array and an imaging strip. The system may be operated in different modes to acquire two-dimensional (2D) images using the imaging array and panoramic images using the imaging strip.

Imaging systems used in dental panels may perform a panoramic imaging operation where an imaging strip is irradiated as the detector rotates around the patient's head. This imaging strip can be integrated as part of a large-format flat panel detector. The image is generated by rapidly scanning the unused rows of the detector, an operation referred to as "scrubbing," and only turning on particular rows of the panel for image readout. This approach suffers from two problems. First, the frame rate is limited by the time it takes to scrub the unused pixels. Second, the imaging may be dose rate limited in particular applications such as medical imaging and thus, background electronic noise has a greater impact on image quality due to the lower available signal.

Conventionally, an array can be about 16×16 centimeters (cm) in size with pixel sizes of approximately 100 micrometers (μm). The matrix of pixels is addressed by a set of gate drivers and read out by an orthogonal set of readout charge amplifiers. Full size images may be acquired by sequentially turning on each row of TFTs and simultaneously reading out the pixel charges on each of the array's data lines. For panoramic mode, the row drivers are controlled to rapidly scan through a first portion of the matrix until the first row of the imaging strip. The row drivers are controlled to slow down to normal readout rate for the duration of the rows of the imaging strip, which may be about 60-100 rows, and then rapidly scan through the remainder of the gate lines to scrub the rest of the imager. Charge readout is normally performed using timing where the gate on-pulse of each pixel is compensated by the gate off-pulse of the previous row's pixel. Other readout methods are possible, but this approach may increase gate on-time to decrease lag and provides relatively flat dark images. Due to the relatively long length of the data lines, the charge amplifiers are set to high power in order to minimize noise from the data line capacitances.

As will be described in further detail below, embodiments include different configurations of imaging arrays and imaging strips. In some embodiments, a separate imaging array and a separate imaging strip may be disposed in the same housing and share common electronics. In other embodiments, the imaging array and the imaging strip may be disposed on the same substrate. In other embodiments, the imaging strip may be a subset of the imaging array with various configurations of connections within the imaging array.

Figure 1:
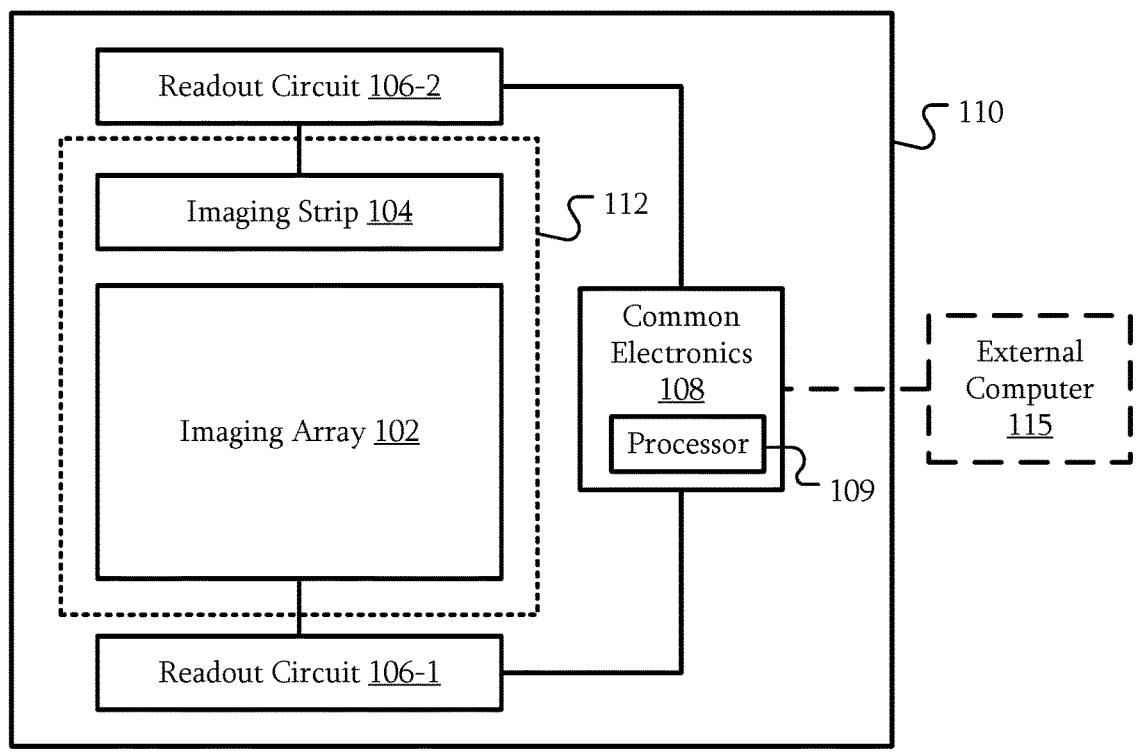
FIG. 1 is a block diagram of an imaging system including an imaging array and an imaging strip according to some embodiments.

FIG. 1 is a block diagram of an imaging system including an imaging array and an imaging strip according to some embodiments. The imaging system 100 includes an imaging array 102 and an imaging strip 104. The imaging array 102 and imaging strip 104 are disposed in the same housing 110.

The imaging array 102 may be a two-dimensional (2D) array of pixels. For example, the imaging array 102 may include a 1600×1600 array of pixels. While an imaging array 102 with equal numbers of pixels in rows and columns has been used as an example, in other embodiments, the number of rows and columns may be different. While a particular number of pixels has been used as an example, in other embodiments, the number of pixels may be different. An aspect ratio of the shorter dimension to the longer dimension in pixels is greater than 0.3, 0.5, 0.75, or the like or equal to 1.

The imaging strip (or linear imaging array or linear array) 104 is an array of pixels with a relatively low aspect ratio, which may or may not be a 2D array. For example, the imaging strip 104 may include an array of 1 pixel×1600 pixels. In other embodiments, the imaging strip 104 may include an array of about 80 pixels×1600 pixels. In other embodiments, the aspect ratio of the shorter dimension to the longer dimension is less than about 0.05, 0.1, or 0.3.

The imaging array 102 and the imaging strip 104 may be based on the same, similar, or different technology. For example, the imaging array 102 may include an amorphous silicon (a-Si) based array while the imaging strip may be based on higher cost and/or higher resolution complementary metal oxide semiconductors (CMOS), indium gallium zinc oxide (IGZO), or a photon counting technology, such as cadmium telluride (CdTe), cadmium zinc telluride (CdZnTe or CZT), selenium photodetectors, or the like. In some embodiments, one or both of the imaging array 102 and the imaging strip 104 may be based on IGZO.

In some embodiments, one or both of the imaging array 102 and the imaging strip 104 may be associated with one or more scintillators. The scintillator(s) may include a variety of materials configured to convert x-ray photons into photons detectable by the corresponding imaging array 102 or imaging strip 104. For example, a scintillator may include cesium iodide (CsI), cadmium tungstate ($CdWO_4$), polyvinyl toluene (PVT), or the like. Other examples of a scintillator include gadolinium oxysulfide ($Gd_2O_2S$; GOS; Gadox), gadolinium oxysulfide doped with terbium ($Gd_2O_2S$:Tb), or the like In some embodiments, the one or both of the imaging array 102 and the imaging strip may not include a scintillator but may include direct conversion materials including CdTe, CdZnTe or CZT, selenium, or the like.

Pixels of the imaging array 102 and the imaging strip 104 may be the same, similar, or different. One or more of the size, layout, spacing, internal components, internal electrical connections, or the like of the pixels may be the same or different. For example, the imaging array 102 may include 50 micrometer (μm) pixels for better single shot accuracy while the imaging strip 104 may have 100 μm pixels for better signal-to-noise ratio and/or faster speed. In another example, one of the imaging array 102 and the imaging strip 104 may have 1T pixels while the other has 4T pixels. While particular examples of differences between the pixels have been used as examples, in other embodiments, the pixels may have other differences.

The imaging system 100 includes a readout circuit 106-1 coupled to the imaging array 102. The readout circuit 106-1 may include one or more amplifiers (e.g., charge amplifiers) for columns of the imaging array 102. In some embodiments, the readout circuit 106-1 may include a charge amplifier for each of the columns of the imaging array 102. As will be described in further detail below, each pixel of a column may be coupled to a data line that is coupled to an input of one of the charge amplifiers of the readout circuit 106-1.

The imaging system 100 includes a readout circuit 106-2 coupled to the imaging strip 104. The readout circuit 106-2 may include one or more charge amplifiers for columns of the imaging strip 104. In some embodiments, the readout circuit 106-2 may include a charge amplifier for each of the columns of the imaging array 102. As will be described in further detail below, each pixel of a column may be coupled to a data line that is coupled to an input of one of the charge amplifiers of the readout circuit 106-2.

The readout circuit 106-1 may be different from the readout circuit 106-2. For example, data lines coupling the pixels of the imaging array 102 to the readout circuit 106-1 may be longer than data lines coupling the pixels of the imaging strip 104 to the readout circuit 106-2 (e.g., due to the larger number of pixel rows). Accordingly, the readout circuit 106-2 may have a different configuration, may be operated differently, or the like due to the lower capacitance of the associated data lines. Although the length of the data lines has been used as an example of why the readout circuit 106-2 may be different, the readout circuit 106-2 may be different for other reasons.

The imaging system 100 includes common electronics 108 coupled to the first readout circuit 106-1 and the second readout circuit 106-2. The common electronics 108 are configured to generate image data in response to at least one of the first readout circuit 106-1 and the second readout circuit 106-2. In some operations, the common electronics 108 generates the image data based on the data from the readout circuit 106-1. In other operations, the common electronics 108 are configured to generate the image data based on the data from the readout circuit 106-2. In other operations, the common electronics 108 is configured to generate the image data based on both the data from the readout circuit 106-1 and the data from the readout circuit 106-2.

The common electronics 108 may include a variety of different circuits shared between the imaging array 102 and the imaging strip 104, and the readout circuits 106-1 and 106-2. For example, the common electronics 108 may include a power supply configured to generate power for the imaging array 102 and the imaging strip 104, and the readout circuits 106-1 and 106-2. The common electronics 108 may include a processor 109, configured to control various operations described herein. Such a processor 109 may be a general purpose processor, a digital signal processor (DSP), an application specific integrated circuit, a microcontroller, a programmable logic device, discrete circuits, a combination of such devices, or the like. The processor 109 may include internal portions, such as registers, cache memory, processing cores, or the like, and may also include external interfaces, such as address and data bus interfaces, interrupt interfaces, or the like. Although only one processor 109 is illustrated in the common electronics 108, multiple processors 109 may be present. In addition, other interface devices, such as logic chipsets, hubs, memory controllers, communication interfaces, or the like may be part of the system common electronics 108 to connect the processor 109 to internal and external components such as the imaging array 102 and the imaging strip 104, the readout circuits 106-1 and 106-2, and an external computer 115.

The external computer 115 is an example of a device that may be coupled (e.g., via wired, optical, or wireless connection) to the imaging system 100 to receive image data from the common electronics 108. The common electronics 108 may be configured to receive and respond to commands from the external computer 115, exchange data with the external computer 115, or the like. The external computer 115 may take a variety of forms such as a desktop computer, server, workstation, tablet computer, mobile device, user interface terminal, or the like.

In some embodiments, the imaging array 102 and the imaging strip 104 are separate. The imaging array 102 and the imaging strip 104 may be disposed on separate substrates that are each attached to the housing 110. The imaging array 102 and the imaging strip 104 may be disposed such that incident radiation may enter a common window or opening 112 and be detected by either the imaging array 102 or the imaging strip 104.

In some embodiments, the imaging strip 104 may have a configuration that results in lower noise, a higher framerate, higher resolution, or the like than the imaging array 102. Accordingly, the imaging array 102 and imaging strip 104 may be used for different applications. As the imaging array 102 and imaging strip 104 are disposed in the same housing 110, a user may use a single imaging system 100 for the different applications or a user may use a detector in a single housing 110 in various imaging systems.

In some embodiments, the imaging array 102 and the imaging strip 104 may not be in operation at the same time. As a result, the common electronics 108 may be used exclusively for the operation of one of the imaging array 102 and the imaging strip 104 at a time. The operation of the common electronics 108 may be different for each of the imaging array 102 and the imaging strip 104. For example, the common electronics 108 may drive row drivers for the imaging strip 104 at a faster rate than those of associated with the imaging array 102.

Figure 2:
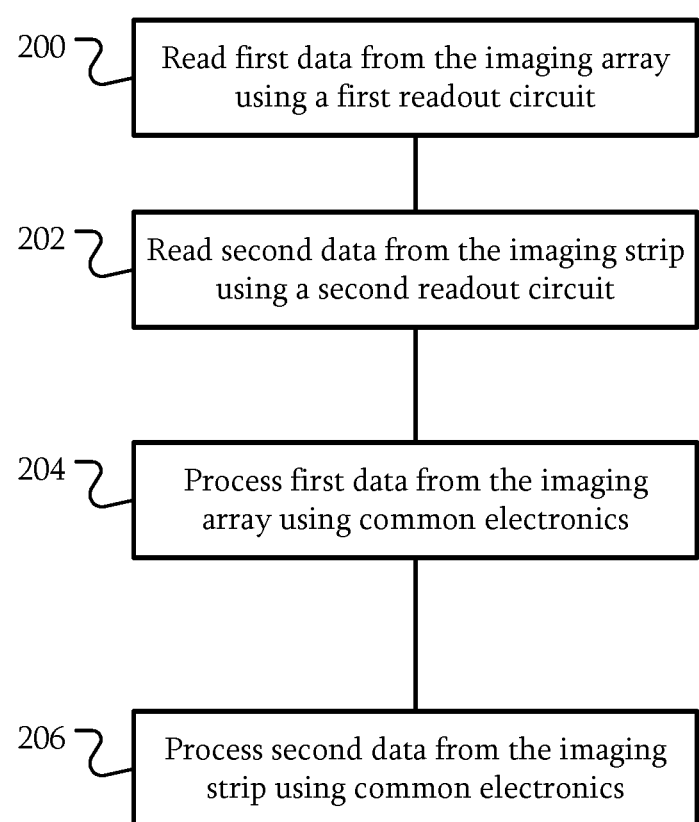
FIG. 2 is a flowchart of an operation of an imaging system according to some embodiments.

FIG. 2 is a flowchart of an operation of an imaging system according to some embodiments. Referring to FIGS. 1 and 2 and using the imaging system 100 as an example, in some embodiments, first data is read from the imaging array 102 using the readout circuit 106-1 in 200. For example, row drivers associated with the imaging array 102 may be sequentially activated to read out data from the imaging array 102 row by row using the readout circuit 106-1. The common electronics 108 may be configured to control of the row drivers and the readout circuit 106-1 to read out the desired data.

In 202, second data is read from the imaging strip 104 using the readout circuit 106-2. For example, row drivers associated with the imaging strip 104 may be sequentially activated to read out data from the imaging strip 104 row by row using the readout circuit 106-2. The common electronics 108 may also be configured to control the row drivers and the readout circuit 106-2 to read out the desired data.

In 204 and 206, data from the imaging array 102 and the imaging strip 104 are respectively processed in the common electronics 108 to generate different sets of image data. The processing in the common electronics 108 in 204 and 206 may be the same, similar, or different. For example, the data from the imaging strip 104 may be processed in a manner to generate image data that results in reduced noise as compared with the processing of the data from the imaging array 102. In other examples, data from the imaging array 102 may be used to generate a video stream while data from the imaging strip 104 may be used to generate a panoramic image. The processing in 204 and 206 may be performed at the same time, in parallel, sequentially, or the like.

While a particular order of operations has been used as an example in FIG. 2, in some embodiments, the order may be different. For example, 204 may be performed before 202. In another example, 200 and 204 may be performed after 206.

Figure 3:
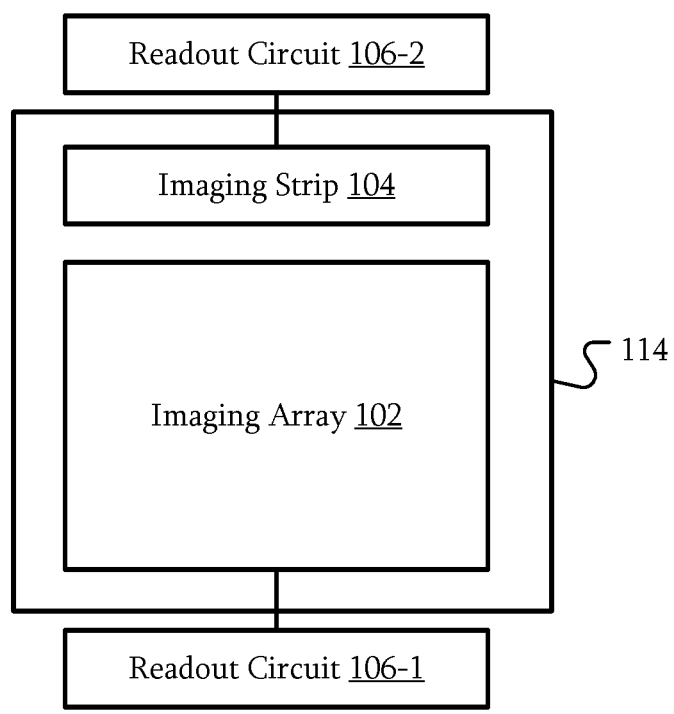
FIG. 3 is a block diagram of an imaging system including a substrate according to some embodiments.

FIG. 3 is a block diagram of an imaging system including a substrate according to some embodiments. The imaging system 300 may be similar to the imaging system 100 of FIG. 1 and include the same or similar components. For clarity, some components are omitted, but may be present. As described above, in some embodiments, the imaging array 102 and the imaging strip 104 may be separate and formed on different substrates. In some embodiments, the imaging system 300 includes a substrate 114. The substrate 114 may be a single substrate formed of such as glass, plastic or polymer, ceramic, an organic or inorganic semiconductor, or the like. The imaging array 102 and the imaging strip 104 may be formed in or on the substrate 114. For example, the imaging array 102 and the imaging strip 104 may be separate integrated circuit dies that are attached to the substrate 114. In other embodiments, the imaging array 102 and the imaging strip 104 may be formed in different portions of the same integrated circuit die, such as in different portions of a semiconductor substrate.

In some embodiments, the imaging array 102 and the imaging strip 104 may still be separate electronic devices, even if the imaging array 102 and the imaging strip 104 are immediately adjacent to one another on the same semiconductor substrate. That is, the imaging array 102 and the imaging strip 104 may have no electrical connections to each other except for parasitic connections through the substrate and/or connections through the readout circuits 106-1 and 106-2 and the common electronics 108.

In some embodiments, the readout circuits 106-1 and 106-2 may be formed on substrates different from the substrate 114. However, in other embodiments, one or both of the readout circuits 106-1 and 106-2 may be formed on the substrate 114.

Figure 4:
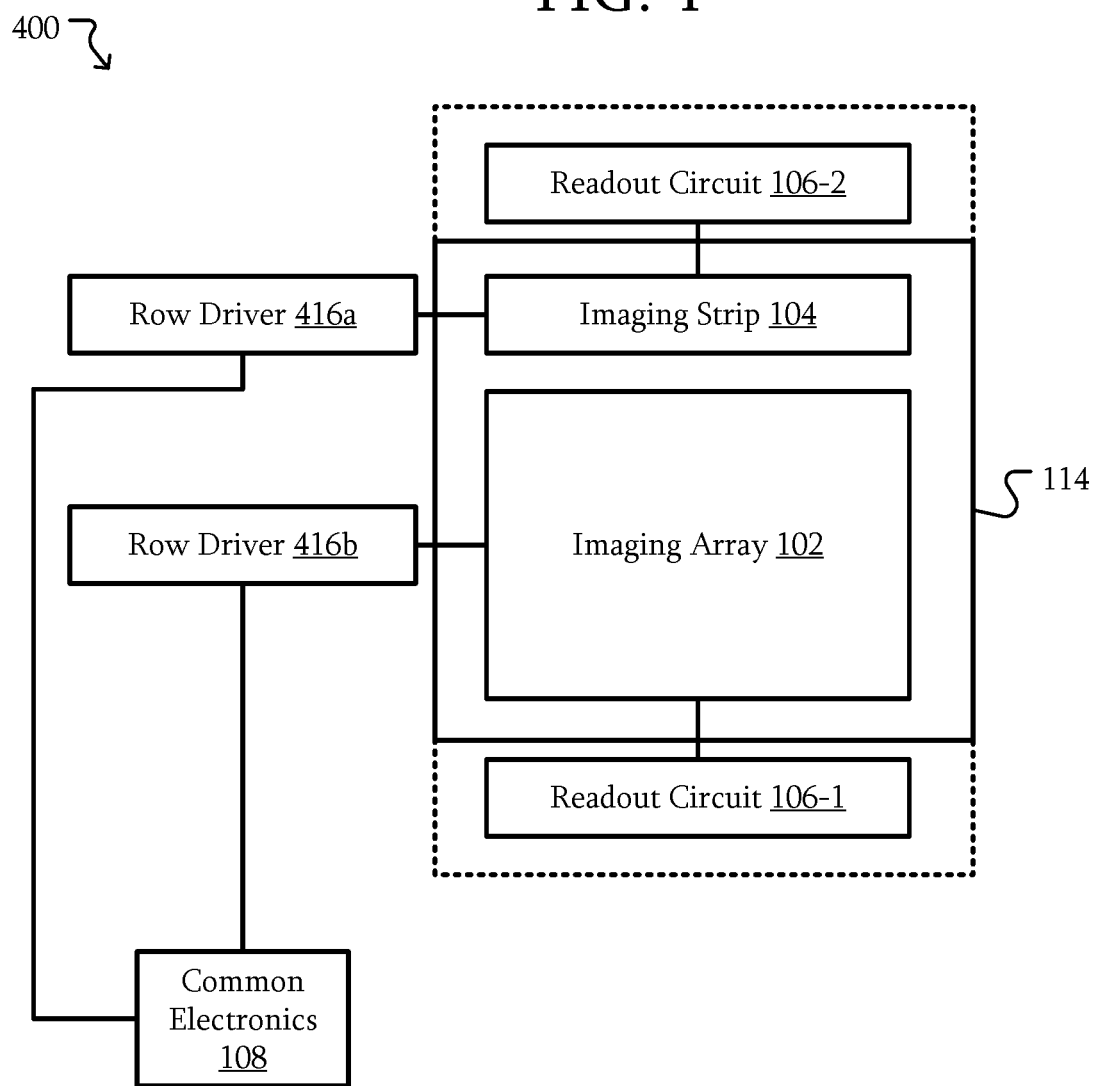
FIG. 4 is a block diagram of an imaging system with separate row drivers according to some embodiments.

FIG. 4 is a block diagram of an imaging system with separate row drivers according to some embodiments. The imaging system 400 may be similar to the imaging system 100 and 300 described above. However, the imaging array 102 is coupled to row driver 416b while the imaging strip 104 is coupled to the row driver 416a. In some embodiments, the row drivers 416a and 416b are separate circuits while in others, the row drivers 416a and 416b are part of the same integrated circuit as the corresponding imaging strip 104 or imaging array 102 or both. The row drivers 416a and 416b may be coupled to and controlled by the common electronics 108.

The row driver 416a is configured to be sequentially activated to read out the imaging strip 104 row by row. The row driver 416b is configured to be sequentially activated to read out the imaging array 102 row by row. The common electronics 108 may be configured to change the signals, timing, or the like when controlling the row driver 416a as compared to when controlling the row driver 416b.

Figure 5:
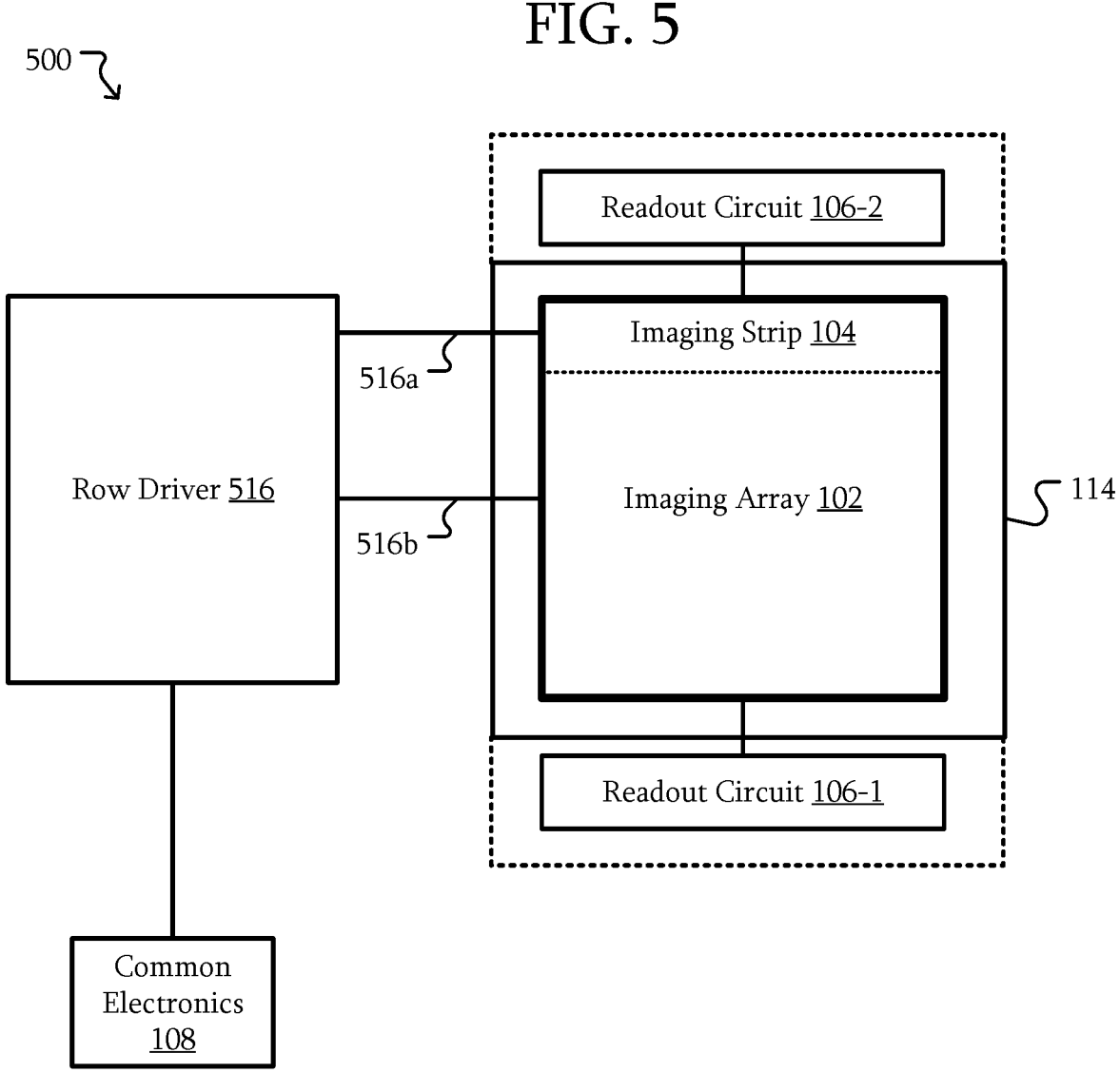
FIG. 5 is a block diagram of an imaging system where an imaging strip is a subset of an imaging array according to some embodiments.

FIG. 5 is a block diagram of an imaging system where an imaging strip is a subset of an imaging array according to some embodiments. The imaging system 500 may be similar to the imaging systems 100, 300, and 400 described above. However, the imaging strip 104 is a subset of the imaging array 102. In some embodiments, the imaging strip 104 may be disposed on an edge of the imaging array 102. For example, the imaging array 102 may have a size of 1600 pixels×1600 pixels. The imaging strip may include the top 80 rows of pixels of the array for a size of 1600 pixels×80 pixels. While a particular size of the imaging strip 104 has been used as an example, the size may be different while maintaining the aspect ratio described above.

In some embodiments, the imaging array 102 may be coupled to row drivers 516. The row drivers 516 coupled to the imaging strip 104 portion of the imaging array 102 may be shared. When the imaging strip 104 is used to generate an image, the associated row select lines 516a may be used. When the imaging array 102 is used to generate an image, all of the row select lines 516a and 516b may be used.

In some embodiments, the pixels of the imaging strip 104 may be identical to and formed the same as the pixels of the remainder of the imaging array 102. For example, the pixels of the imaging strip 104 may have the same size, shape, pitch, or the like. Conventionally, pitch refers to the pixel length or width along with the spacing between pixels. As a result, when an image is generated using the imaging array 102, an artifact may not appear due to a discontinuity between the imaging strip 104 and the remainder of the imaging array 102.

In some embodiments, when reading the image array 102, the row driver 516 is configured to progressively activate the row select lines 516a and 516b across the imaging array 102.

Figure 6:
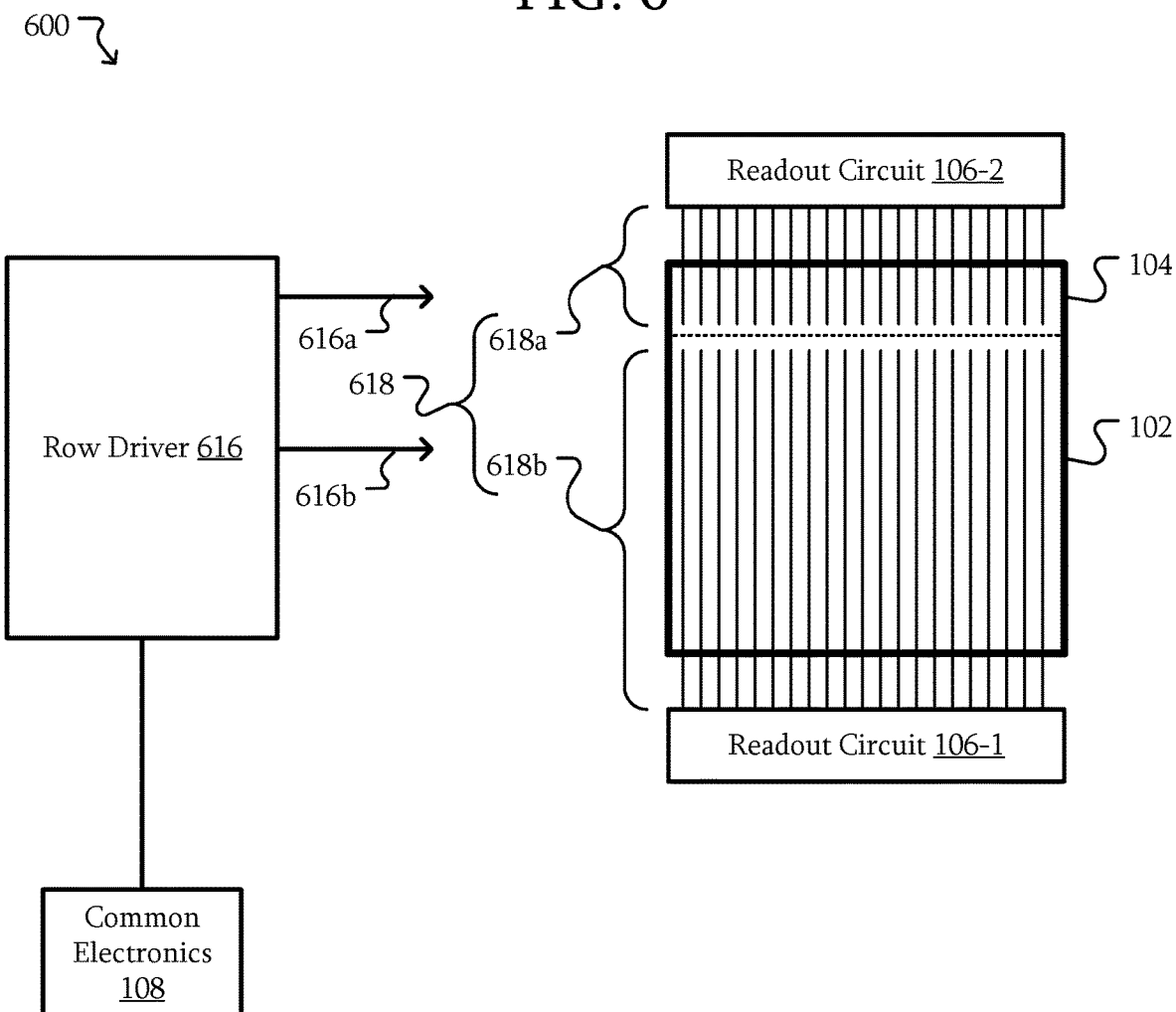
FIG. 6 is a block diagram of an imaging system with split data lines according to some embodiments.

FIG. 6 is a block diagram of an imaging system with split data lines according to some embodiments. The imaging system 600 may be similar to the imaging system 500 as described above, or the like. The imaging system 600 includes split data lines 618. The data lines 618 are split into two groups, data lines 618a and data lines 618b. Data lines 618a are coupled to the imaging strip 104 portion of the imaging array 102 and coupled to readout circuit 106-2. Data lines 618b are coupled to the remainder of the imaging array 102 and coupled to readout circuit 106-1.

The location of the split between the data lines 618a and 618b may be in a variety of locations. In some embodiments, the split is about 30% of the column length where the date lines 618a are coupled to 30% of pixels in a column while data lines 618b are coupled to 70% of pixels in a column. While 30% is used as an example, in other embodiments, the location may be different, such as a split at 1%, 5%, 10%, 20%, or the like. In other embodiments, split may be at a particular number of pixels from an edge, such as about 80 pixels or less, but still less than 30% of the number of pixels in a column of the imaging array 102. In some embodiments, the split may be located such that only pixels of the imaging strip 104 are coupled to the data lines 618a while pixels outside of the imaging strip 104 are coupled to the data lines 618b. In other embodiments, some pixels outside of the imaging strip 104 are coupled to the data lines 618a but the total number of pixels of a column coupled to the data lines 618a may be less than about 30%.

Having the split at less than about 30% provides benefits for the imaging strip 104. In some embodiments, the noise may be less as the data lines 618a are shorter than the data lines 618b. In some embodiments, that lower noise may cause artifacts to appear in an image generated using the imaging array 102; however, as will be described in further detail below, additional noise or an equivalent may be added to the data generated by the imaging strip 104 when the entire imaging array 102 is used to generate an image. In some embodiments, the downstream processing may be different. For example, a different dark level matching operation may be performed as compared with the remainder of the imaging array 102.

In some embodiments, an amount of noise reduction and/or increase in signal to noise ratio may be about 10%, 20%, 40%, 50%, or more. For example, the shorter data lines 618a results in a lower data line capacitance and resistance, which may reduce electronic readout noise. In a particular example, charge amplifiers may have a minimum noise of about 200 electrons (e−), that increases linearly with added data line capacitance. The noise slope is controlled by the power applied to the charge amplifiers and the bandwidth setting of associated sample and hold circuits. In addition, the resistance of the data lines produces thermal noise, or Johnson noise, that gets multiplied by the data line capacitance. This Johnson noise increases with length but may be negligible for shorter data lines such as data lines 618a coupled to the imaging strip 104. The resulting noise may be close to the minimum noise of the charge amplifier in combination with the kTC noise of the pixel. This noise (estimated to be 400 e−) may be about 40% less than the noise from an array of the same size where the data lines are not split (approximately 700 e−). The term kTC noise refers to noise generated by temperature (T) and capacitance (C) multiplied by the Boltzmann constant (k), such as thermal noise multiplied by the data line capacitance and the Boltzmann constant. The Boltzmann constant (k) is a proportionality factor that relates the average relative kinetic energy of particles with the thermodynamic temperature of the particles.

The shorter length may also increase readout speed. For example, fewer rows may be read during a read operation of the pixels of the imaging strip 104. The remainder of the imaging array 102 need not be scrubbed to read the pixels of the imaging strip 104. Using 80 rows of pixels for the imaging strip 104 as an example, the control logic 103 may continue passing tokens (i.e., signals that propagate along the row driver 616 to activate the rows) into the row driver 616 every 80 gate clocks to activate the row select signals 616a. These tokens may pass though the remaining row drivers 616 and scrub the rest of the imaging array 102 using row select signals 616b without interfering with the readout of the imaging strip 104. This may increase readout speed of the imaging strip 104. For example, assuming the rate for scrubbing pixels is about 1 microsecond (μs) per row, then the time it takes to scrub a 1600 row imaging array 102 outside of an 80 row imaging strip 104 (about 1520 rows) is about 1.52 milliseconds (ms). Assuming about 16 μs to readout each row of the imaging strip 104, an 80 row imaging strip 104 takes 1.28 ms to readout. The total time is about 2.8 ms resulting in a maximum frame rate of 357 fps. In the case of a dedicated imaging strip 104, the readout time is just the 1.28 ms resulting in a frame rate of about 780 fps. In a predetermined number of frames, such as 19 frames, of readout (24 ms), the remaining pixels in the array may be scrubbed.

In some embodiments, the readout circuits 106-1 and 106-2 may be the same and/or operated the same way while in other embodiments, the readout circuits 106-1 and 106-2 may be different and/or operated differently. For example, the readout circuits 106-1 and 106-2 may be identical. In other embodiments, the readout circuits 106-1 and 106-2 are identical but operated differently, such as having different gain, current, capacitance, or the like. In other embodiments, the readout circuits 106-1 and 106-2 may be different where the readout circuits 106-2 are optimized for the shorter data lines 618a.

Referring to FIGS. 2 and 6, in some embodiments, in 200, the reading of the first data from the imaging array 102 includes reading the first data from the imaging array 102 through data lines 618b. In 202, reading the second data from the imaging strip 104 includes reading the second data from the imaging strip 104 using data lines 618a that are different from the data lines 618b.

Figure 7A:
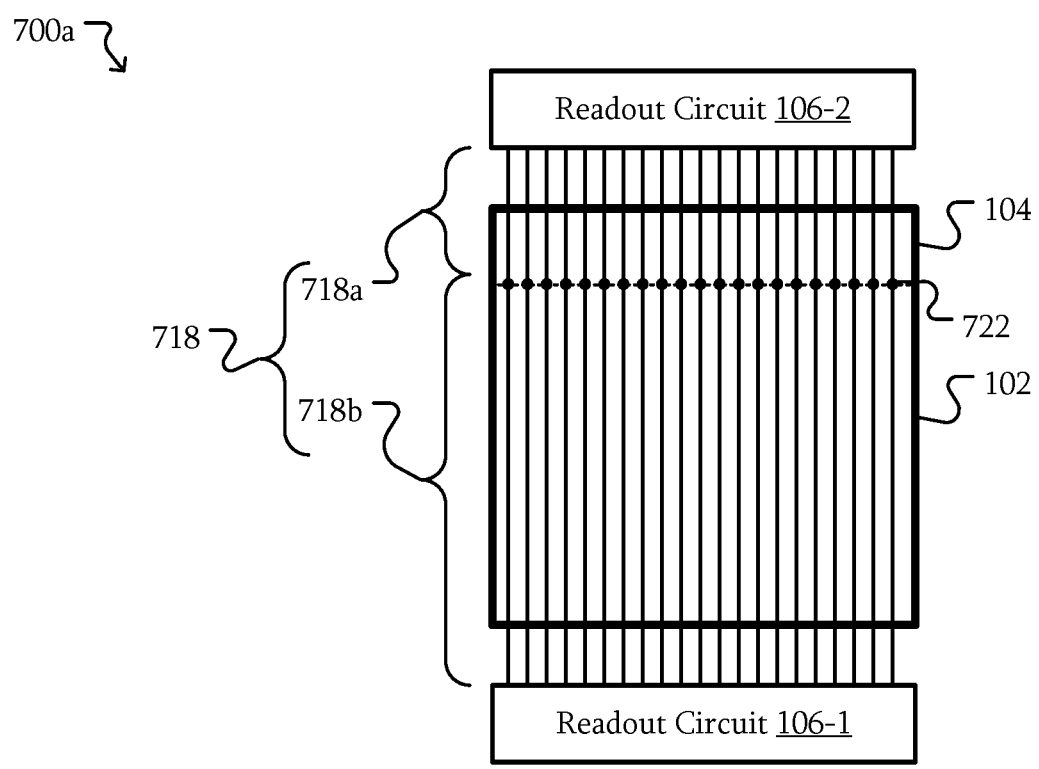
FIGS. 7A-7B are block diagrams of imaging systems with selectively couplable split data lines according to some embodiments.
Figure 7B:
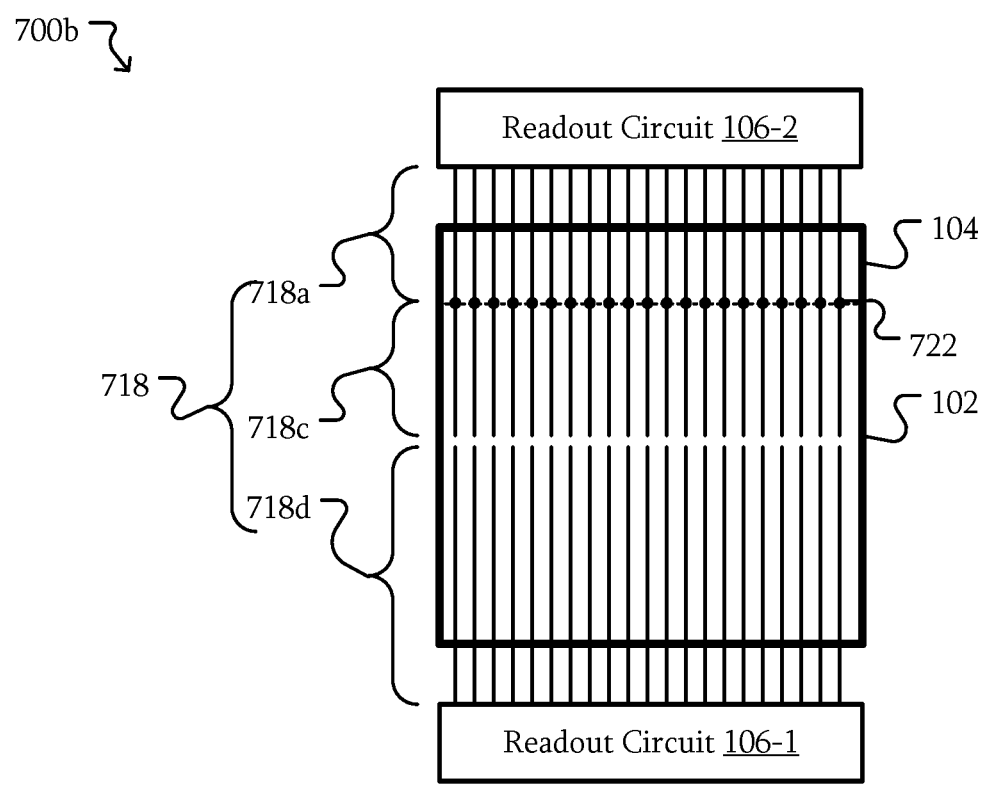

FIGS. 7A-7B are block diagrams of imaging systems with selectively couplable split data lines according to some embodiments. Referring to FIG. 7A, the imaging system 700a may be similar to the imaging system 600 described above. However, the system 700a incudes data lines 718a coupled to the imaging strip 104, data lines 718b coupled to a remainder of the imaging array 102. The data lines 718a and 718b are separate but selectively couplable by switches 722. Each of the switches 722 may selectively couple one of the data lines 718a to the corresponding data line 718b.

In some embodiments, the switches 722 may include one or more transistors coupling the data lines 718a and 718b. The switches 722 may be controlled by the control logic 103 such that when the imaging strip 104 is read, the switches 722 are open. As a result, lower capacitances from the data lines 718a alone are presented to the readout circuit 106-2.

However, when the imaging array 102 is read, the data lines 718a and 718b may be coupled together to function as single data lines. The data from the imaging array 102 may be read through the coupled data lines 718a and 718b through the readout circuit 106-1.

Referring to FIG. 7B, the imaging system 700b may be similar to the imaging system 700a. However, the data lines associated with the imaging array 102 may include the data lines 718a, 718c, and 718d. In some embodiments, a split between the data lines 718c and 718d may be at 50% of the distance along the imaging array 102. For example, 50% of the pixel rows may be on one side of the split between the data lines 718c and 718d and 50% of the pixel rows may be on the other side of the split.

The data lines 718a and 718c may be selectively couplable by the switches 722 in response to the control logic 103. In some embodiments, the imaging strip 104 may be read by using the switches 722 to decouple the data lines 718a and the 718c and reading using the readout circuit 106-2 through the data lines 718a. When reading the imaging array 102, the data lines 718a and 718c may be coupled by the switches 722 and read using the readout circuit 106-2 through the combination of the data lines 718a and 718c. The remainder of the imaging array 102 may be read through the data lines 718d using the readout circuit 106-1. The coupling of the data lines 718a and 718c may occur at less than 50% of the of the pixel rows or data lines 718a may cover less than 30% of the entire imaging array 102.

Accordingly, in various embodiments, a portion of the data lines of the entire imaging array 102 may be decoupled from the data lines 718a associated with the imaging strip 104. That portion may be a subset of the remainder outside of the imaging strip 104 or the entire remainder as in the imaging systems 700a and 700b.

Referring to FIGS. 2, 7A, and 7B, in some embodiments, in 200, reading the first data from the imaging array 102 includes electrically coupling the first data lines 718a or 718c to the second data lines 718b when reading the first data from the imaging array 102. In 202, reading the second data from the imaging strip 104 includes electrically decoupling the first data lines 718a or 718c from the second data lines 718b when reading the second data from the imaging strip 104.

Figure 8A:
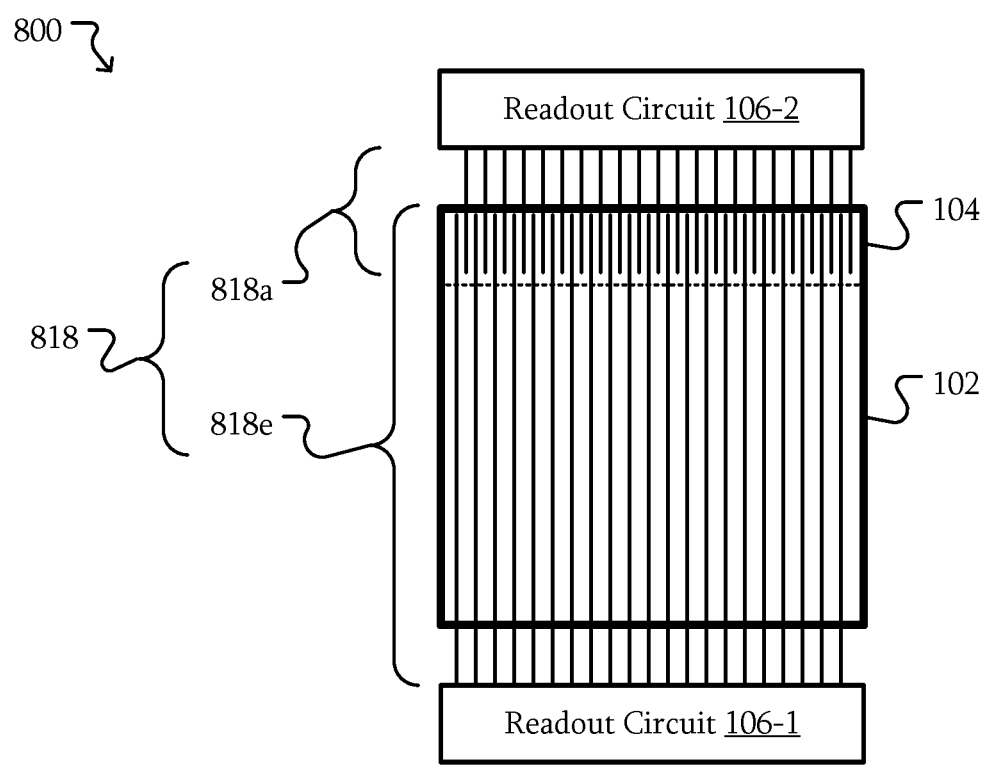
FIGS. 8A-8B are block diagrams of imaging systems with multiple data lines according to some embodiments.
Figure 8B:
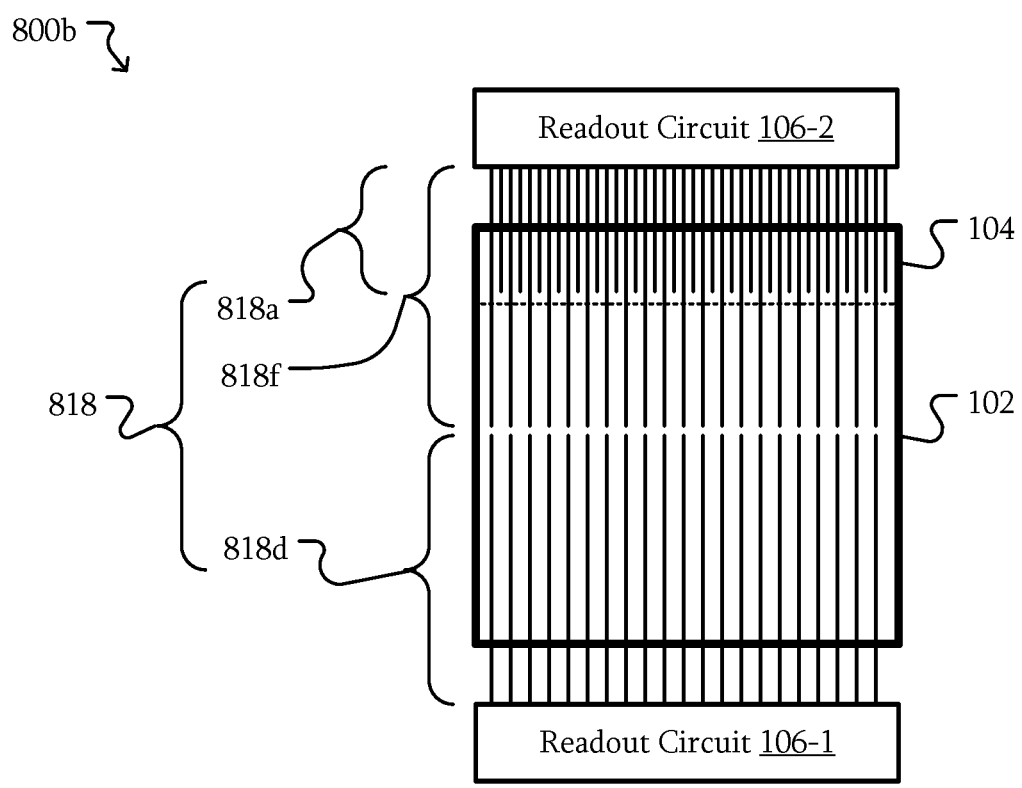

FIGS. 8A-8B are block diagrams of imaging systems with multiple data lines according to some embodiments. The imaging system 800a may be similar to the imaging systems 500 and 600 described above. However, the imaging system 800a includes data lines 818a and 818e. The data lines 818a are coupled to pixels of the imaging strip 104. The data lines 818e are coupled to pixels of the entire imaging array 102 including the pixels of the imaging strip 104. Thus, at least two data lines 818a and 818e are coupled to each pixel of the imaging strip 104. Accordingly, when the imaging strip 104 is read, data lines 818a are used while when the imaging array 102 is read, data lines 818e are used.

Referring to FIG. 8B, in some embodiments, the imaging system 800b may be similar to the imaging system 800a. In some embodiments, the data lines for the imaging array 102 may include split data lines 818d and 818f, which are split halfway along the imaging array 102. The readout circuit 106-2 may include separate inputs for the data lines 818a and 818f. The readout circuit 106-1 may be coupled to the data lines 818d. Accordingly, when the imaging strip 104 is read, data lines 818a are used while when the imaging array 102 is read, data lines 818d and 818f are used.

As described above, in various embodiments, an amount of noise present in data read from the imaging strip 104 may be less than an amount of noise present in data read from the remainder of the imaging array 102. For example, the data lines used to read data from the imaging strip 104 may be shorter than data lines used to read data from the imaging array 102. Those data lines may have less capacitance and contribute less noise. In some applications, the reduced noise may be desirable. For example, the reduced noise present when reading the imaging strip 104 may allow a lower dose to be used for the same signal to noise ratio in the resulting image, a higher signal for the same dose, a different tradeoff among the various factors the two, or the like.

If the data from the imaging strip 104 is combined with data from the imaging array 102, even if the pixels of each have the same characteristics, an artifact may appear due to the different noise level. To compensate for this, the readout circuit 106-2 may be operated in a manner that increases an amount of noise read from the imaging strip 104. For example, built-in test capacitors, external capacitors, or other capacitors may be selectively coupled to the inputs of the readout circuit 106-2, a power of one or more amplifiers may be reduced, and/or the bandwidth of components of the readout circuit 106-2, such as the amplifiers and/or sample and hold circuits may be increased. These operations may add electronic noise and can be adjusted to match the overall noise between the imaging strip 104 and the rest of the imaging array 102. For example, a typical 20 µs line time may use 40 kilohertz (kHz) low pass filters for noise reduction. For the majority of the image readout on data lines with capacitance on the order of tens of picofarads (pF), with the readout circuit 106-1 set to high power low noise conditions, the electronic noise is about 600-800 e⁻. For the imaging strip 104 to achieve noise of this level, a low power normal noise mode of operation may be used, test capacitors having capacitances similar to that of the data lines that are built into the readout circuit 106-2 are coupled to the data lines, and/or the bandwidth is increased to 105 kHz. This operation gives a similar overall noise in the imaging strip 104 strip of about 600-800 e⁻. Although particular examples of techniques to add noise, simulate noise, equalize noise, or the like have been described above, in other embodiments, other operations may be performed to reduce or eliminate an artifact in an image due to the lower noise of the imaging strip 104.

In some embodiments, the imaging systems described above, 400, 600, 700a, 700b, 800a, 800b, or the like may be operated in a mode where power may be managed dynamically. For example, in operation, the control logic 103 may be configured to control amplifiers of a readout circuit 106-1 or 106-2 to operate in a higher power mode to reduce noise when reading the entire imaging array 102. However, when reading the imaging strip 104, the amplifiers of the readout circuit 106-2 may be operated in a lower power mode. While the lower power mode of operation may increase the relative amount of noise and/or decrease signal-to-noise ratio (SNR), the power consumption is lower. In addition, the amplifiers of the readout circuit 106-1 may be turned off, put in a sleep mode with significantly lower power consumption, or the like. When the entire imaging array 102 may be read, the readout circuits 106-1 and 106-2 may be placed in the higher power mode to reduce the impact of noise. Dynamically switching between these modes of operation may reduce the power consumption of the imaging system 500, 600, 700a, 700b, 800a, 800b, or the like, reduce the temperature, and/or improve the reliability.

In some embodiments, an impact of pixel kTC noise in an image may be reduced. As a result, a lower dose may be used to achieve a desired resolution, a frame rate may be increased, or the like.

Figure 9A:
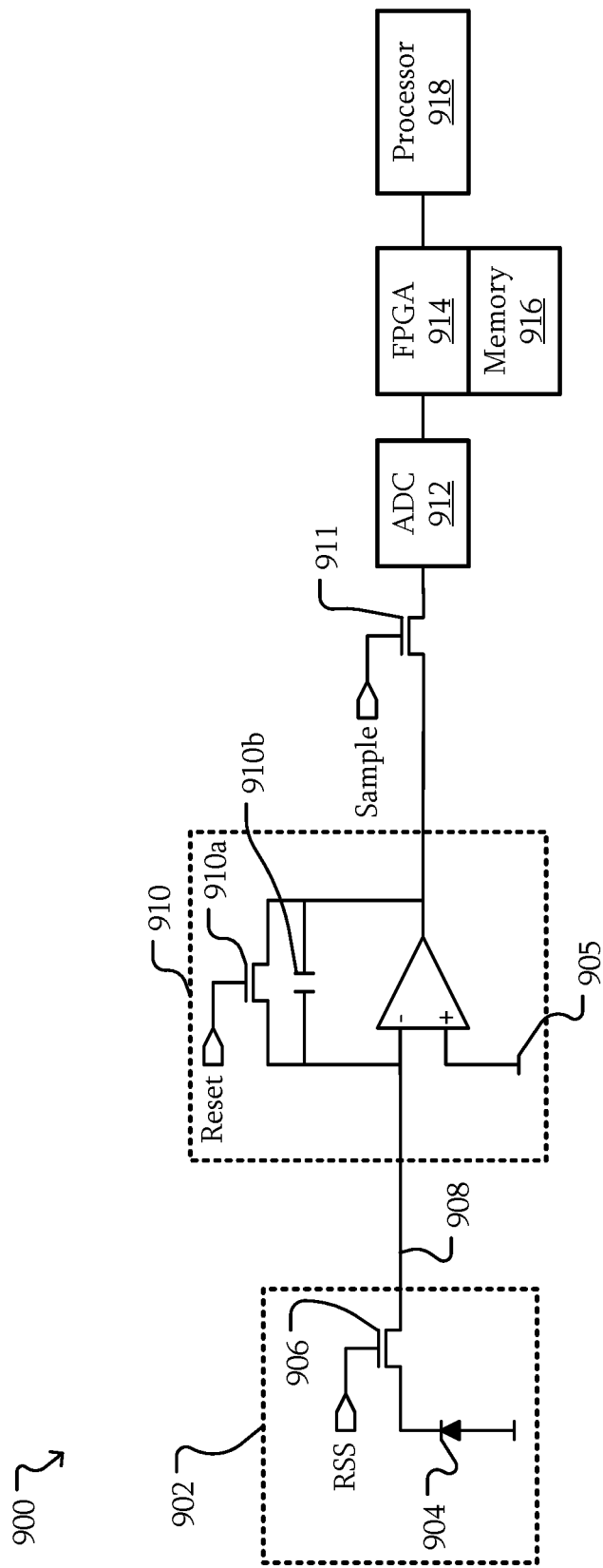
FIG. 9A is a block diagram of a pixel and associated electronics in an imaging system according to some embodiments.

FIG. 9A is a block diagram of a pixel and associated electronics in an imaging system according to some embodiments. FIG. 9B is a block diagram of an imaging array and associated electronics in the imaging system according to some embodiments. Referring to FIGS. 9A and 9B, the imaging system 900 includes pixels 902 disposed in rows and columns.

A pixel 902 includes a photodetector 904 (e.g., photodiode) and a transistor 906 (i.e., switch). The transistor 906 is configured to selectively couple the photodetector 904 to a data line 908 in response to a row select signal (RSS). Multiple pixels 902 may be coupled to a single data line 908 in a column.

The data line 908 is coupled to an amplifier 910. In some embodiments, the amplifier 910 is an integrating amplifier including a reset transistor (or reset switch) 910a and a charge storage device 910b, such as a capacitor. The reset transistor 910a is configured to reset the amplifier 910 in response to a reset signal Reset. The output of the amplifier 910 may be selectively coupled to an analog to digital converter (ADC) 912 through a select transistor 911 in response to a sample signal Sample. The digitized signal may be processed by a field-programmable gate array (FPGA) 914, stored in the memory 916, and/or further processed by the processor 918 or other downstream systems.

Control logic 903 may be coupled to the various components described above. For example, the control logic 903 may be coupled to row drivers 901. The control logic may be configured to control the row drivers 901 to generate the row select signals RSS for the rows of the pixels 902. The control logic 903 may be configured to configured and control the operations of the ADC 912, FPGA, 914, processor 918, or the like. The control logic 903 may include a general purpose processor, a digital signal processor (DSP), an application specific integrated circuit, a microcontroller, a programmable logic device, discrete circuits, a combination of such devices, or the like. The control logic 903 may include internal portions, such as registers, cache memory, processing cores, or the like, and may also include external interfaces, such as address and data bus interfaces, interrupt interfaces, or the like. In addition, other interface devices, such as logic chipsets, hubs, memory controllers, communication interfaces, or the like may be part of the imaging system 900 to connect control logic 903 to internal and external components.

While the control logic 903 is illustrated as separate from the FPGA 914, processor 918, or the like, the control logic 903 may be integrated with such components. For example, the control and/or the performance of operations described herein may be distributed across the FPGA 914, the processor 918, a combination of such components, or the like.

Figure 10:
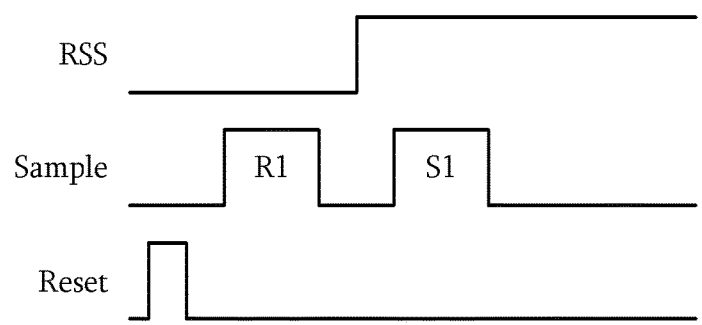
FIG. 10 is a timing diagram of a double sampling operation.

FIG. 10 is a timing diagram of a double sampling operation. Referring to FIGS. 9A, 9B, and 10, the system 900 may be operated according to the timing diagram of FIG. 10. For example, the transistor 910a may be enabled to reset the amplifier 910 in response to the pulse on the reset signal Reset. During this operation, the transistor (or switch) 906 is disabled as the row select signal RSS is disabled. The sample signal Sample is activated while the row select signal RSS is disabled to sample the reset value at the output of the amplifier 910 as After acquiring the value $R_1$, the sample signal Sample is deactivated. After deactivating the sample signal Sample, the row select signal RSS is enabled, enabling the transistor 906. As a result, charge from the photodetector 904 accumulates in the amplifier 910. The sample signal Sample is enabled to sample the value $S_1$ at the output of the amplifier 910.

Equations 1 and 2 show the components of the sampled values $R_1$ and $S_1$. $V_{reset}$ is the sampled reset voltage including noise contributed by the amplifier 910. $V_{signal,pixel}$ is the desired signal from the pixel 902. $V_{kTC}(N-1)$ is the pixel kTC noise left over from the previous reading of the pixel 902. $V_{dataline}$ noise is the noise due to the data line 908.

$$R_1 = V_{reset} \tag{1}$$

$$S_1 = V_{reset} + V_{signal,pixel} - V_{kTC}(N-1) + V_{dataline\ noise} \tag{2}$$

Equation 3 is the difference between $R_1$ and $S_1$, $V_{p1}(N)$. The result includes the desired signal, $V_{signal,pixel}$, along with the pixel kTC noise, $V_{kTC}(N-1)$, and the data line noise $V_{data\ line}$.

$$V_{p1}(N) = S_1 - R_1 = V_{signal,pixel} - V_{kTC}(N-1) + V_{dataline\ noise} \tag{3}$$

The operation of equation 3 may be performed in a variety of ways, such as by analog correlated double sampling (ACDS), digital correlated double sampling (DCDS), or other processes that would subtract the signals $R_1$ and $S_1$.

Fixed pattern noise sources may be caused by pixel-to-pixel or amplifier-to-amplifier variation. Fixed pattern noise may not change from frame to frame. However, pixel kTC noise is generated by resistance in the pixel semiconductor switch and stored on the capacitance of the photodetector 904. The pixel kTC noise may vary from frame to frame. Fixed pattern noise can be reduced through manufacturing control. The reduction of pixel kTC noise can be made by reducing the capacitance of the photodetector 904 by reducing the size of the photodetector 904; however, reducing the size of the photodetector 904 may reduce other factors, such as sensitivity, efficiency, or the like.

The result in equation 3 still has the pixel kTC noise. The pixel kTC noise may be reduced by changes to the pixel design such as adding additional transistors. However, pixels formed using some semiconductor technologies, such as in amorphous silicon (a-Si), the size of the transistors may be prohibitive. For example, a single transistor may take up a significant percentage of a pixel for a given pixel size. Adding more transistors would significantly reduce the pixel area available for the photodetector 904, reducing the efficiency of the system 900.

As will be described in further detail below, the system 900 may be operated differently, reducing the pixel kTC noise. In some embodiments, a measurement may be performed where the pixel kTC noise may be acquired and used to reduce or eliminate the pixel kTC noise from a signal measurement. Although pixel kTC noise varies from frame to frame, the pixel noise kTC noise is presented to the input of the amplifier 910 (and subsequently output) from the amplifier 910 after the signal sample is taken and the transistor 906 is disabled by disabling the row select signal RSS. At this point in the operation, a sample may be acquired to capture the kTC noise. This sample may be stored and then used to reduce or eliminate the pixel kTC noise from the signal from the pixel 902 in the next frame.

That measurement may then be used to remove or reduce the pixel kTC noise in the final value. Thus, a measurement from a previous frame is used to reduce or cancel pixel kTC noise in a current frame. Although embodiments described herein may be applicable to systems using a-Si process or other processes where a size of a transistor may be relatively large compared to a pixel size, in other embodiments, systems may be formed using other processes, such as complementary metal oxide semiconductor (CMOS) processes.

Figure 11A:
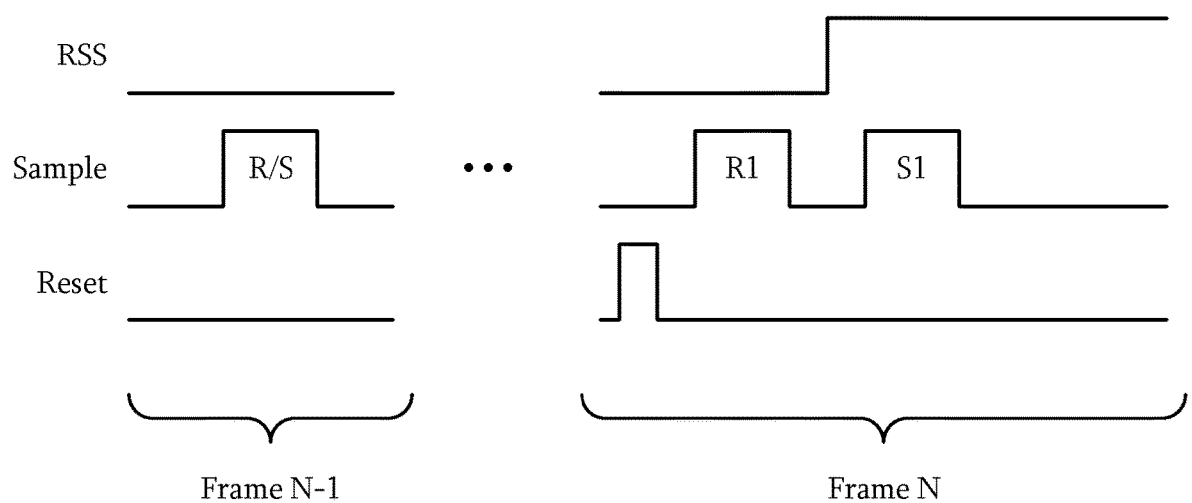
FIG. 11A is a timing diagram according to some embodiments.
Figure 11B:
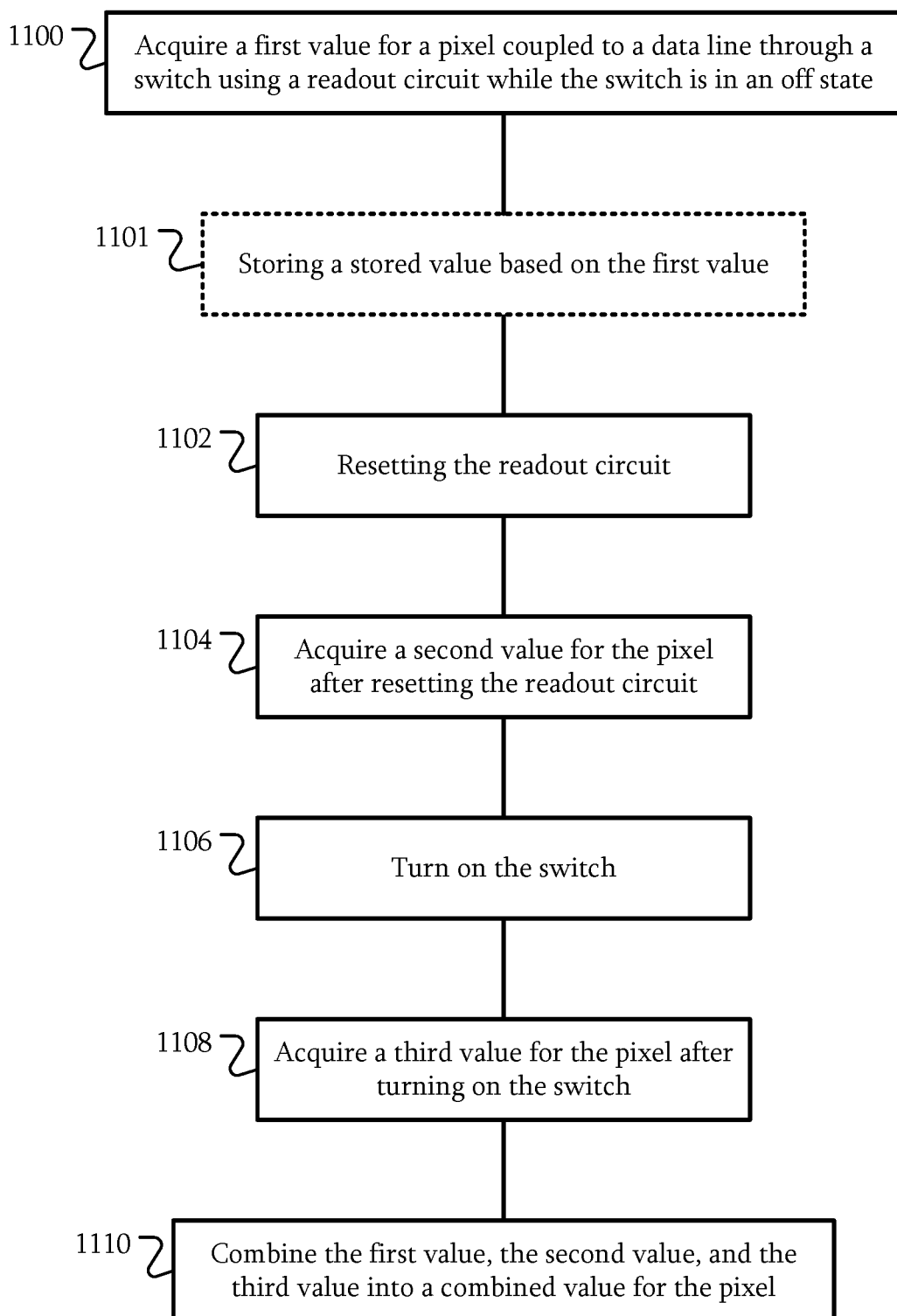
FIG. 11B is a flowchart of an operation of an imaging system according to some embodiments.

FIG. 11A is a timing diagram according to some embodiments. FIG. 11B is a flowchart of an operation of an imaging system according to some embodiments. Referring to FIGS. 9A, 9B, 11A, and 11B, in 1100 a first value for a pixel 902 coupled to a data line 908 is acquired through a switch using a readout circuit while the switch is in an off state. Here, the transistor 906 is an example of the switch and the readout circuit includes the amplifier 910 and at least some downstream components. This first value, a sample R/S is acquired in an N−1-th frame, while the transistor 906 is disabled. Subsequent processing may occur before later operations are performed for frame N.

In 1102 the readout circuit is reset. In this example, the amplifier 910 is reset. However, in other embodiments, additional components may be reset. Resetting the amplifier 910 may include discharging the charge storage device 910b by activating the rest signal Reset.

In 1104, a second value for the pixel 902 is acquired after resetting the readout circuit. In this example, the value $R_1$ is acquired after resetting the amplifier 910.

In 1106, the switch is turned on. Here, the row select signal RSS is activated, turning on the transistor 906. As a result, charge from the pixel 902 may be transferred to the amplifier 910.

In 1108 a third value for the pixel 902 is acquires after turning on the switch. In this example, the value $S_1$ is acquired after turning on the transistor 906.

In 1110 the first value, the second value, and the third value are combined into a combined value for the pixel 902. In this example, the three values $R_1$, $S_1$, and R/S are combined into the combined value for the pixel 920. As will be described in further detail below, the three values $R_1$, $S_1$, and R/S may be combined in various ways to reduce or eliminate pixel kTC noise. The various values combined together may include other values depending on the particular combination technique to combine the first, second, and third values together to reduce or eliminate the kTC noise.

In some embodiments, in 1101, a stored value based on the first value is stored. For example, a value based on the value R/S may be stored in the FPGA 914, the memory 916, the processor, 920, or another downstream system. The stored value is based on the value from the previous frame N−1. The stored value may be combined with the values $R_1$ and $S_1$ from the current frame N. Accordingly, the combination in 1110 may include the combination of the first value by way of the stored value based on the first value. In some embodiments, an entire frame's worth of R/S values or the derived values may be stored for each of the pixels 902. An entire frame's worth of the values $R_1$ and $S_1$, whether separate or combined, may be combined with the stored R/S values.

The operations described herein involve the acquisition of an additional sample during the readout process. As this additional sample takes additional time, the readout time is increased. However, the noise may be reduced, potentially increasing the signal to noise ratio, allowing for a lower dose, or the like. Accordingly, in some embodiments, an increase in readout time may be traded for a decrease in noise, a lower dose, or the like.

In some embodiments, the noise reduction benefit has a greater impact when the data line 908 capacitance is smaller. When the values are combined, the noise from the data line 908 capacitance is increased by the square root of 2. In some embodiments, binning may be implemented during the capture of signals from the pixels 902. For example, in a 2×2 binning mode, four pixels 902 are combined to operate as a single pixel. Relative to the readout of a single pixel 902, the data line 908 noise may be doubled while the pixel kTC noise would otherwise be quadrupled. However, the pixel kTC noise may be reduced or eliminated. Thus, the operations described herein may have a greater impact when binning is performed.

Figure 12A:
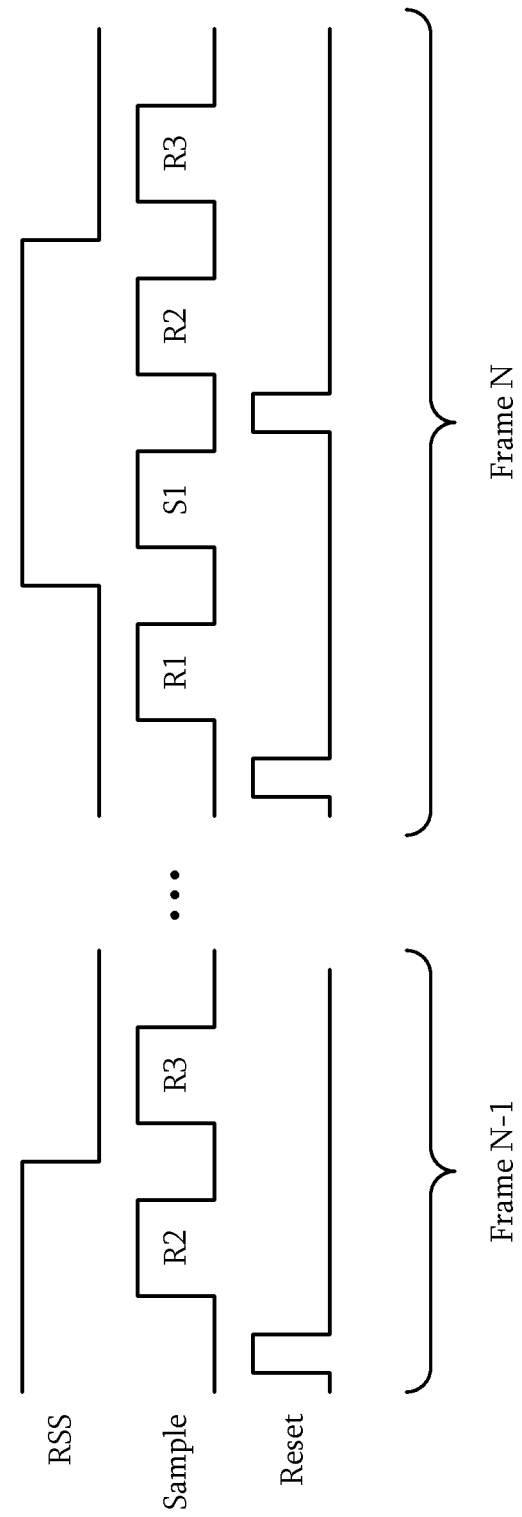
FIG. 12A is a timing diagram according to some embodiments.
Figure 12B:
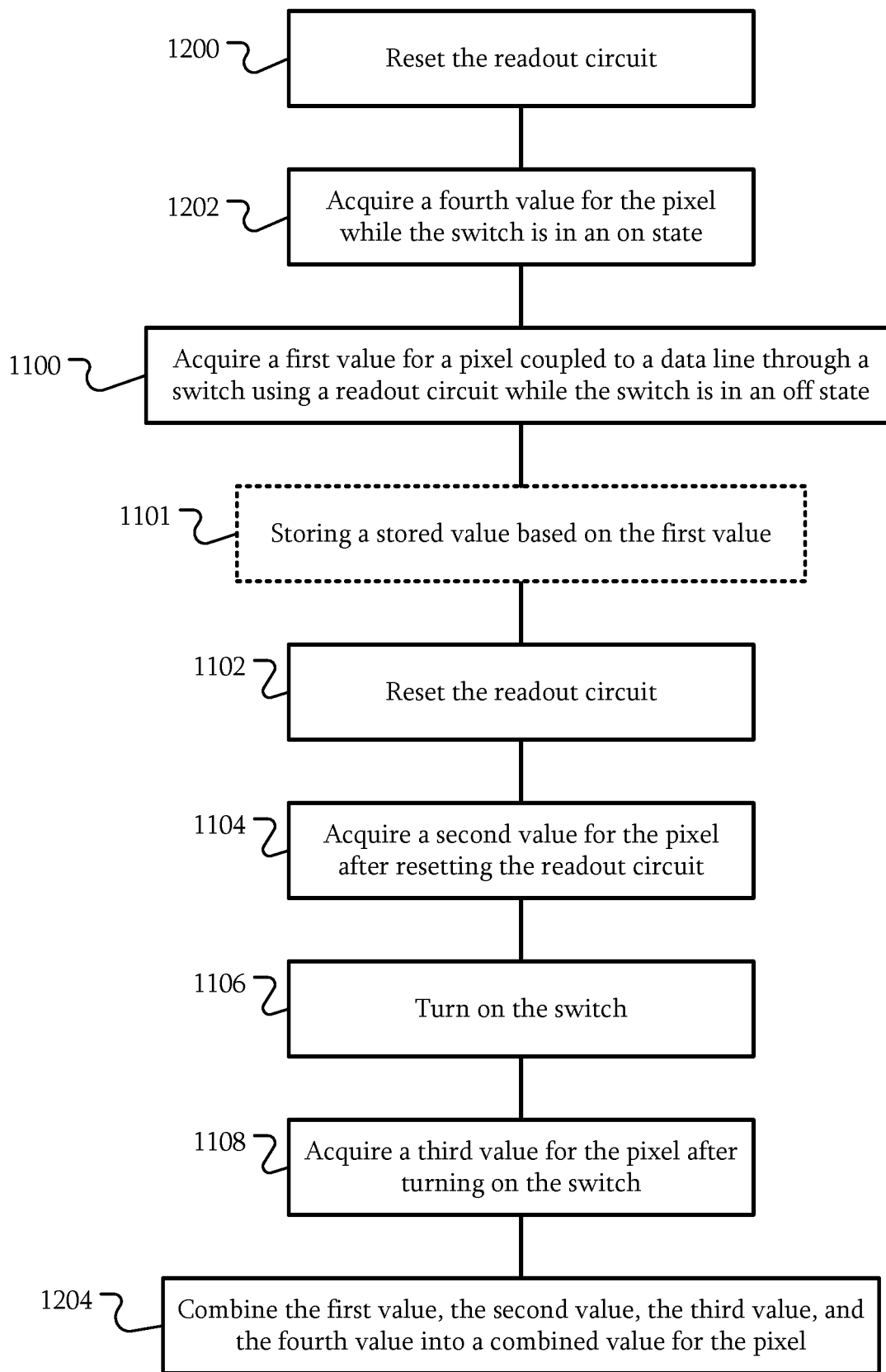
FIGS. 12B-12C are flowcharts of an operation of an imaging system according to some embodiments.
Figure 12C:
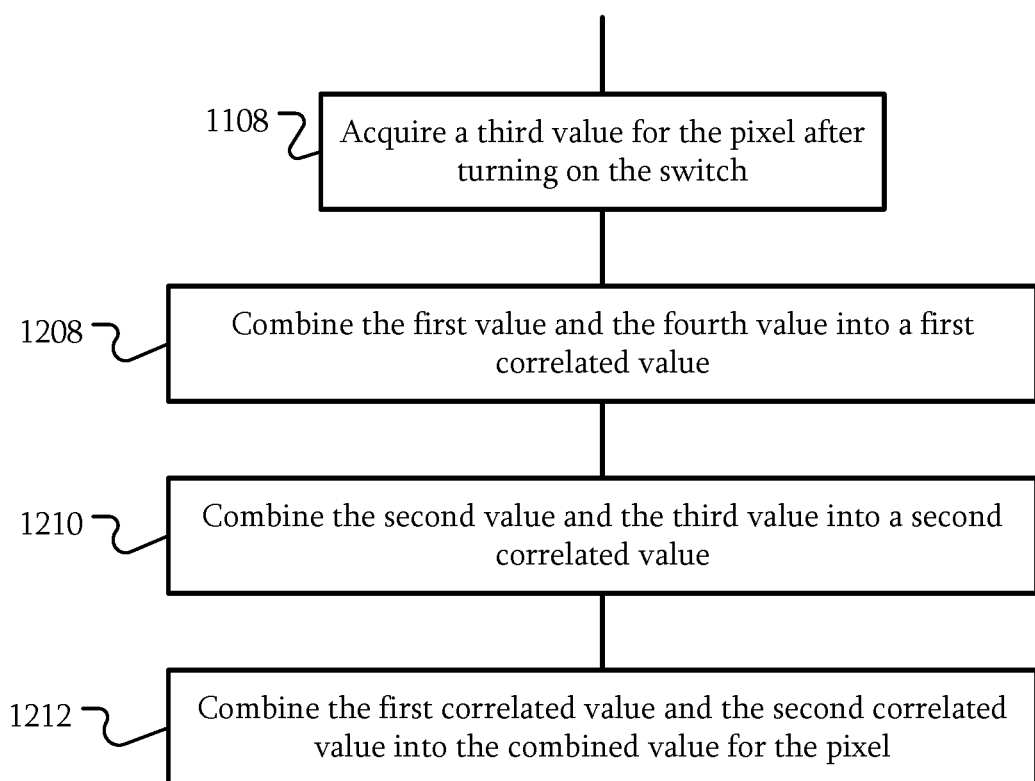

FIG. 12A is a timing embodiment according to some embodiments. FIGS. 12B-12C are flowcharts of an operation of an imaging system according to some embodiments. Referring to FIGS. 9A, 9B, 12A, and 12B, the operation may be similar to that of FIGS. 11A and 11B including the operations 1100, 1101 (optionally) 1102, 1104, 1106, and 1108 being similar to those described above with respect to FIG. 11B. In 1200, before acquiring the first value for the pixel 902, the readout circuit is reset. For example, the amplifier 910 may be reset with a pulse on the reset signal Reset. This operation may be the same or a similar operation to the later performed reset in 1102.

In 1202, a fourth value for the pixel 902 is acquired while the switch is in an on state. For example, after the amplifier 910 is reset, a value $R_2$ is acquired while the switch 906 is in an on state.

The operation continues similar to that of FIG. 11B where $R_3$ is the value R/S. In 1204, the values $S_1$, $R_1$, $R_2$, and $R_3$ are combined together to generate a combined value for the pixel 902. Equations 4-6 show the components of the sampled values $R_1$, $S_1$ and $V_{p1}(N)$ similar to equations 1-3 described above. $V_{reset1}$ is the reset voltage that is sampled after resetting the amplifier 910.

$$R_1 = V_{reset1} \quad (4)$$

$$S_1 = V_{reset1} + V_{signal,pixel} - V_{kTC}(N-1) + V_{dataline\ noise\ 1} \quad (5)$$

$$V_{p1}(N) = S_1 - R_1 = V_{signal,pixel} - V_{kTC}(N-1) + V_{dataline\ noise\ 1} \quad (6)$$

Equation 7 is the sampled value $R_2$. The value $R_2$ is sampled after the amplifier 910 is reset and while the switch 906 is in an on state. Equation 8 is the sampled value at $R_3$. The value $R_3$ is sampled after the switch 906 transitions to an off state. Equation 9 is the difference between $R_2$ and $R_3$. Equation 10 is $V_{pixel}(N)$, the sum of $V_{p1}(N)$ and $V_{p2}(N-1)$. While different data line noises $V_{dataline\ noise\ 1}$ and $V_{dataline\ noise\ 2}$ were added, the resulting combination is effectively the square root of two times a generic data line noise level.

$$R_2 = V_{reset2} \quad (7)$$

$$R_3 = V_{reset2} + V_{kTC}(N-1) + V_{dataline\ noise\ 2} \quad (8)$$

$$V_{p2}(N-1) = R_3 - R_2 = V_{kTC}(N-1) + V_{dataline\ noise\ 2} \quad (9)$$

$$V_{pixel}(N) = V_{p1}(N) + V_{p2}(N-1) = V_{signal,pixel} + \sqrt{2} * V_{dataline,noise} \quad (10)$$

The values $R_2$ and $R_3$ that were sampled on the previous frame N−1 have the pixel kTC noise from that previous frame. To explain the values of $R_2$ and $R_3$ from the previous frame N−1, the operations in frame N will be explained. The amplifier 910 is reset and a sample is made after the reset. This generates value $R_1$. The pixel 902 is turned on by turning on switch 906 and another sample is made for the signal, generating value $S_1$. The two samples $R_1$ and $S_1$ are then subtracted as was done before.

After the sample of the signal to generate value $S_1$ is performed the transistor 906 is not opened, but remains in the on state. The amplifier 910 is reset by a pulse on the reset signal Reset and a sample is acquired, value $R_2$. This sample includes the reset value of the amplifier 910. When the switch 906 is opened in response to deactivating the row select signal RSS, the pixel kTC noise is transferred and is integrated by the amplifier 910. In particular, when turning off the transistor 906, some charge remains in the pixel 902 and an equal and opposite amount is integrated by the amplifier 910. This integrated amount is the opposite of the pixel kTC noise that will be present the next time the pixel 902 is read.

The output of the amplifier 910 is sampled again, acquiring value $R_3$, which includes the reset value, the pixel kTC noise and the data line 908 noise. The pixel kTC noise is the pixel kTC noise that will appear the next time the pixel 902 is read in the next frame. Accordingly, when this operation is performed in frame N−1, the values $R_2$ and $R_3$, or a combination of those values may be used for the next frame N.

In some embodiments, the operations of Equations 6 and 9 may be performed by using correlated double sampling techniques. For example, whether analog or digital, a correlated double sampling technique may be used to generate the difference between $R_2$ and $R_3$ as shown in Equation 9. Similarly, at a different time, the correlated double sampling technique may be used to generate the difference between $R_1$ and $S_1$ as shown in Equation 6. Thus, the different values may be combined into two different correlated values. Those correlated values may be combined as in Equation 10. Accordingly, in some embodiments, existing hardware may be used to generate the values $V_{p1}(N)$ and $V_{p2}(N-1)$ by controlling various signals such as the reset signal Reset and row select signal RSS. Rather than two correlated double sampling operations being performed to eventually produce two frames' worth of image data, two correlated double sampling operations may be performed to eventually produce one frame's worth of image data.

Referring to FIGS. 9A, 9B, and 12A-12C, 1204 of FIG. 12B may be replaced with 1208 and subsequent processing. After operations 1200 to 1108, in 1208, the first value and the fourth value may be combined into a first correlated value. As described above, the values $R_2$ and $R_3$ may be combined through a correlated double sampling technique. In 1210, the second value and the third value may be combined into a second correlated value. As described above, $R_1$ and $S_1$ may be combined through a correlated double sampling technique. In 1212, the first correlated value and the second correlated value are combined into the combined value for the pixel 902. The combination may be performed by a variety of devices, such as the FPGA 914, the processor 918, the control logic 903, an external computer 913, or the like.

Figure 13A:
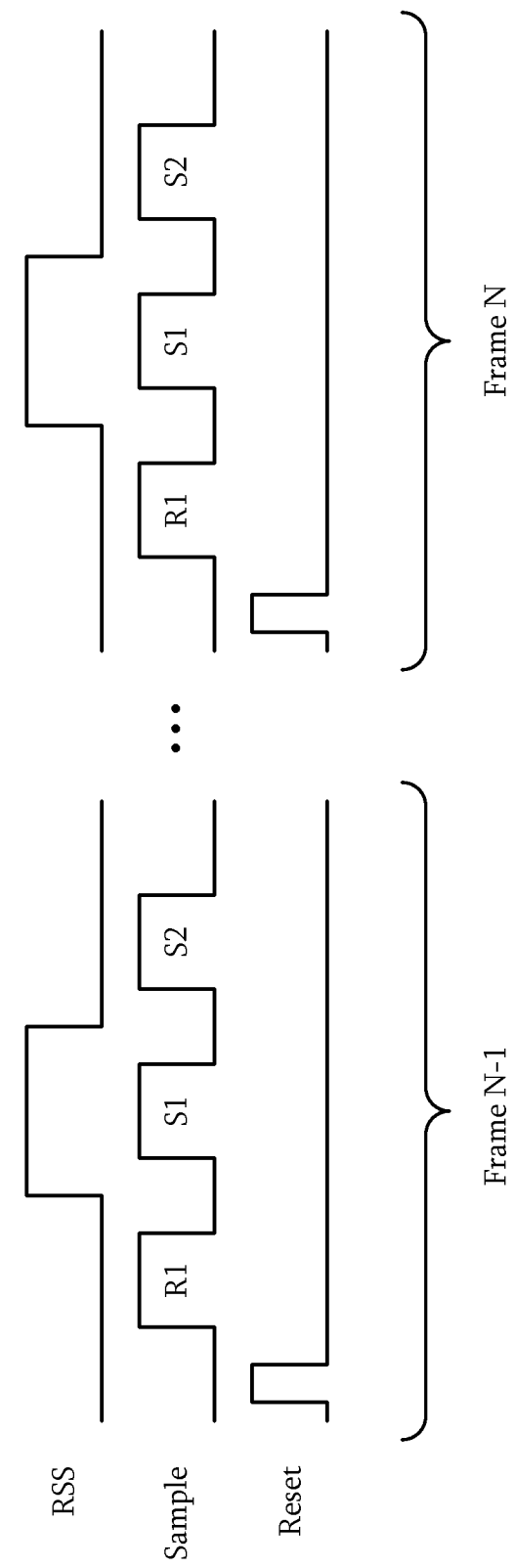
FIG. 13A is a timing diagram according to some embodiments.
Figure 13B:
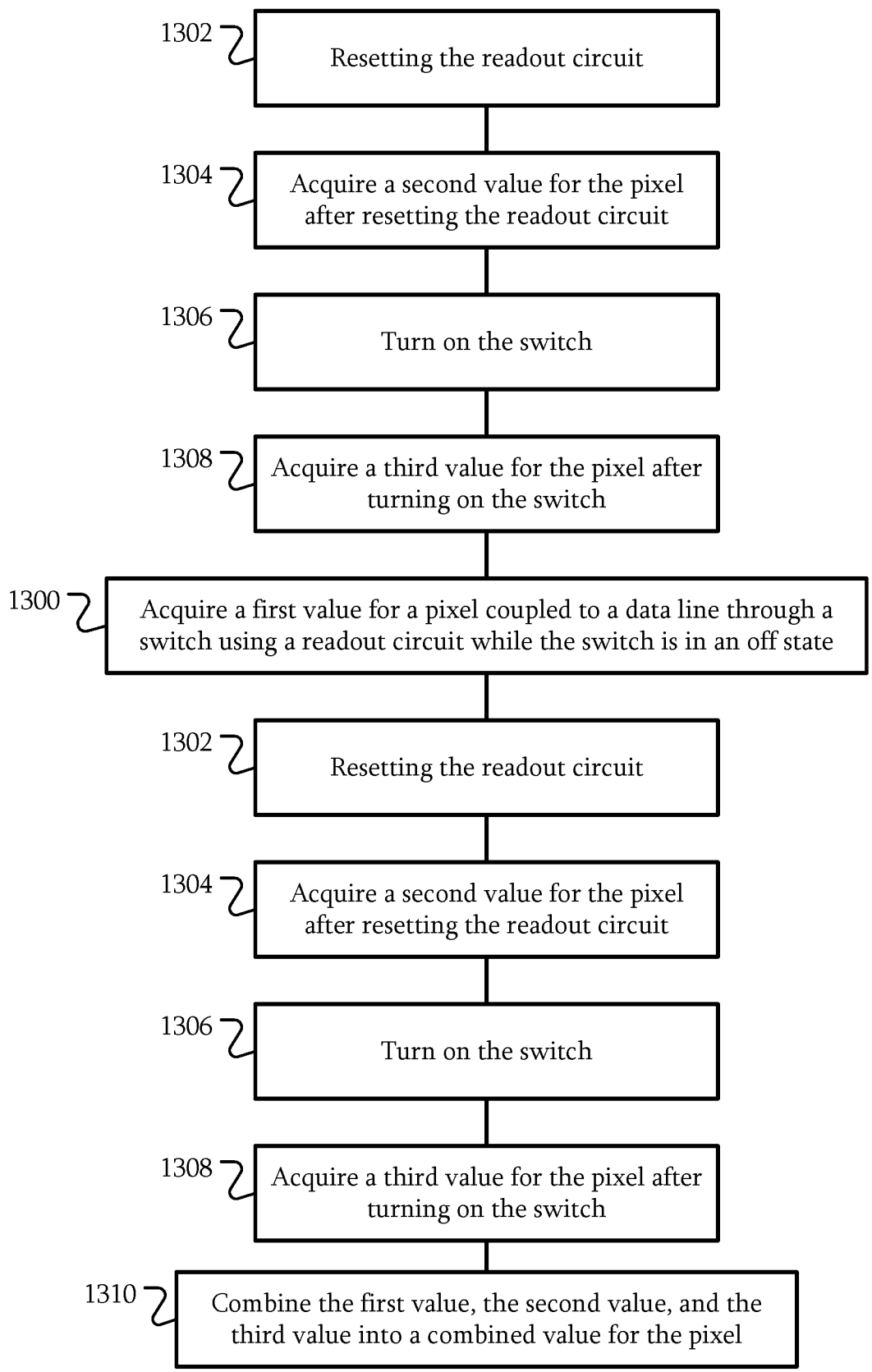
FIG. 13B is a flowchart of an operation of an imaging system according to some embodiments.

FIG. 13A is a timing diagram according to some embodiments. FIG. 13B is a flowchart of an operation of an imaging system according to some embodiments. Referring to FIGS. 9A, 9B, 13A, and 13B, in some embodiments, the signals that generate values $R_1$ and $S_1$ may be similar to those described above. However, a third value $S_2$ based on a previous frame is combined with those values.

In 1302 to 1308, the operations are the same or similar as 1102 to 1108 for FIG. 11B to generate values $R_1$ and $S_1$. These operations are for a previous frame N−1. In 1300, similar to 1100, the first value for the pixel 902 for use in a subsequent frame is acquired without resetting the corresponding readout circuit. For example, when acquiring the first value, the switch is in an off state. Thus, after 1306, the row select signal RSS is disabled, turning off transistor 906. A value $S_2$ is then acquired as the first value for use in the subsequent frame N. At a later time for frame N, operations 1302 to 1308 are repeated, generating the values $R_1$ and $S_1$ for the frame N. Operation 1310 is performed similar to operation 1110 to combine the first value, the second value, and the third value. Operation 1300 may be performed, generating value $S_2$ for frame N for use in frame N+1.

In a particular example, for a previous frame N−1, Equations 11 and 12 give the components of $R_1(N-1)$ and $S_1(N-1)$.

$$R_1(N-1) = V_{reset1} \tag{11}$$

$$S_1(N-1) = V_{reset1} + V_{signal,pixel} - V_{kTC}(N-2) + V_{dataline\ noise\ 1} \tag{12}$$

However, a value $S_2$ is acquired after the value $S_1$ is acquired for the previous frame N−1. That value $S_2$ is acquired after the transistor 906 is turned off and without resetting the amplifier 910. Thus, the resulting value $S_2$ includes both the previously integrated value $S_1$ plus the pixel kTC noise as represented by Equation 13 and simplified in Equation 14.

$$S_2(N-1) = V_{reset1} + V_{signal,pixel} - V_{kTC}(N-2) + V_{kTC}(N-1) + V_{dataline\ noise\ 2} \tag{13}$$

$$S_2(N-1) = S_1(N-1) + V_{kTC}(N-1) + V_{dataline\ noise\ 2} \tag{14}$$

Subtracting $S_1$ from $S_2$ results in the pixel kTC noise for the previous frame N−1 as shown in Equation 15.

$$V_{p,kTC}(N-1) = S_2 - S_1 = V_{kTC}(N-1) + V_{dataline\ noise\ 2} \tag{15}$$

For the current frame N, the values $R_1$ and $S_1$ are acquired and combined as shown in Equations 16-18. The pixel kTC noise from Equation 15 was previously generated. It may be added to $V_{p1}(N)$ to remove the pixel kTC noise from the previous frame N−1.

$$R_1(N) = V_{reset1} \tag{16}$$

$$S_1(N) = V_{reset1} + V_{signal,pixel} - V_{kTC}(N-1) + V_{dataline\ noise\ 1} \tag{17}$$

$$V_{p1}(N) = S_1 - R_1 = V_{signal,pixel} - V_{kTC}(N-1) + V_{dataline\ noise\ 1} \tag{18}$$

$$V_{pixel} = V_{p1} + V_{p,kTC}(N-1) = V_{signal,pixel} + \sqrt{2} * V_{dataline,noise} \tag{19}$$

As only three values are acquired, a speed of processing of a frame of data may be increased beyond that described above with the acquisition of four values. As a result, the framerate may be increased. However, hardware different from existing correlated double sampling hardware may be used. That is, while $S_1$ and $R_1$ may be combined using correlated double sampling techniques to generate a single value representing the difference, the value $S_2$ may use different electronics to generate the value. In addition, the sampling circuitry may be configured to sample the values $R_1$, $S_1$, and $S_2$ separately and combine them in the FPGA 914, the processor 918, an external computer 913, or other downstream system.

Figure 13C:
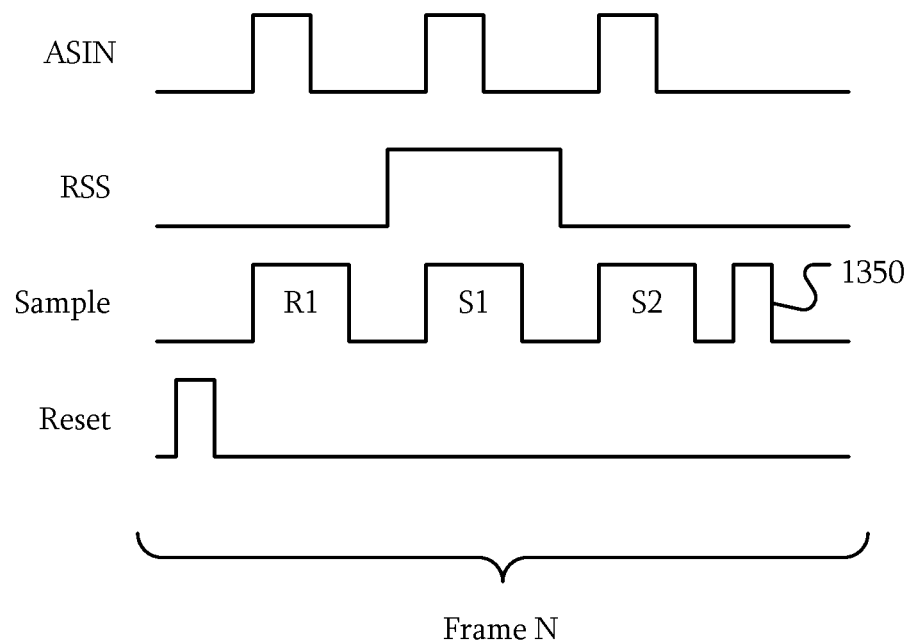
FIG. 13C is a timing diagram according to some other embodiments.

FIG. 13C is a timing diagram according to some embodiments. Referring to FIGS. 9A, 9B, 13B, and 13C, in some embodiments, a digital correlated double sampling technique may be used. In response to an ASIC shift in signal (ASIN), signals to be sampled may be shifted on to sampling capacitors or other sample storage devices. The operation may be similar to that of FIG. 13A. In some embodiments, the sampling capacitors may be a bank of sampling capacitors where the usage of the capacitors is rotated among the sampling operations. Sample signals Sample may be activated as described above to sample values $R_1$, $S_1$, and $S_2$. However, the bank of sampling capacitors may include an even number of sampling capacitors. A fourth sample signal 1350 or additional sample signals may be activated to ensure that the associated pixel 902 sees the same sampling capacitor. While one sample signal 1350 is used as an example, more may be present as needed. The sampled value may be irrelevant. Accordingly, the ASIN may not be activated. Thus, in some embodiments, the number of times that signals are shifted in to be sampled may be less than the number of times the sample signal Sample is activated.

Figure 13D:
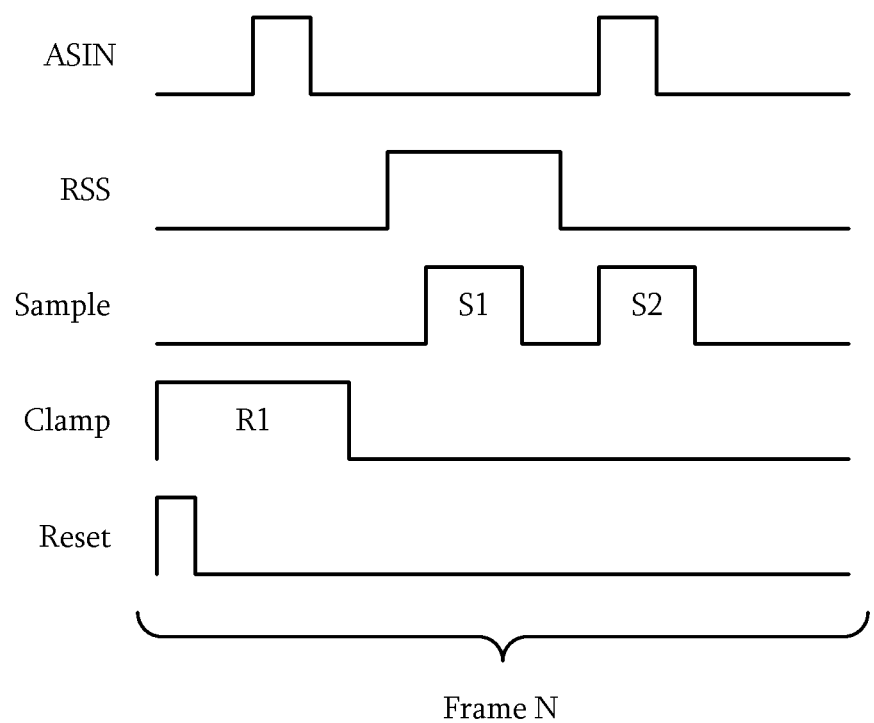
FIG. 13D is a timing diagram according to some other embodiments.

FIG. 13D is a timing diagram according to some embodiments. Referring to FIGS. 9A, 9B, 13B, and 13D, in some embodiments, the operations may be performed using analog correlated double sampling. In response to a clamp signal Clamp a reset value $R_1$ may be stored on a sampling capacitor. That sampling capacitor may be coupled to an analog subtraction device, such as a differential amplifier, that performs the analog subtractions associated with the analog correlated double sampling.

In some embodiments, two measurements are digitized as intermediate values. As described above, in equations 12 and 13, $S_1$ and $S_2$ both include the reset value $R_1$. Rather than directly subtracting $S_1$ and $S_2$, $R_1$ is subtracted through the analog correlated double sampling operation from both $S_1$ and $S_2$ before the samples are digitized. Accordingly, subsequent operations that may be performed digitally may be represented by equations 20-22 where $S'_1$ is the digitized value after $R_1$ was subtracted from $S_1$ in the differential amplifier and $S'_2$ is similarly the digitized value after $R_1$ was subtracted from $S_2$. The resulting $V_{p,kTC}$ in equation 22 may be used as described above.

$$S'_1(N-1) = S_1 - R_1 \quad (20)$$

$$S'_2(N-1) = S_2 - R_1 \quad (21)$$

$$V_{p,kTC}(N-1) = S'_2 - S'_1 = V_{kTC}(N-1) \quad (22)$$

Accordingly, in various embodiments, the acquiring operations of 1300, 1304, 1308, and the combination operation of 1310 may be performed in a variety of combinations of hardware and digital signal processing.

Figure 14:
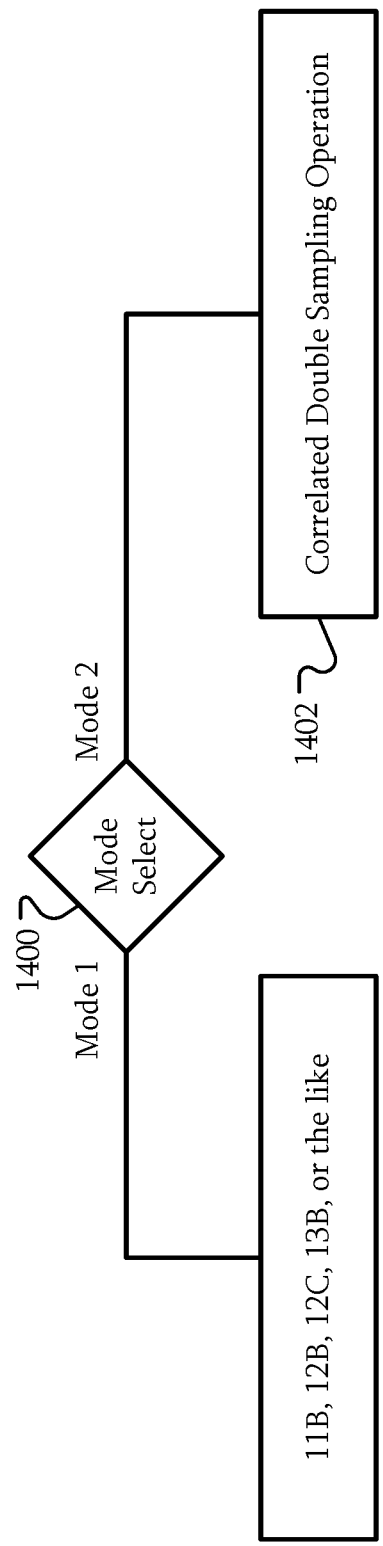
FIG. 14 is a flowchart of a technique of operating an imaging system according to some embodiments.

FIG. 14 is a flowchart of a technique of operating an imaging system according to some embodiments. In 1400, a mode of operation is selected. In a first mode of operation, operations similar those described in FIGS. 11B, 12B, 12C, 13B, or the like as described above may be performed. As a result, lower noise data may be acquired. However, some applications may need a higher framerate. Thus, the additional delay due to the additional samples in the lower noise operation may be undesirable. Accordingly, a second mode of operation may be selected where, in 1402, a correlated double sampling operation is performed. In this mode, the acquisition of the first value is not performed. Accordingly, the operation of the system may be switched from a lower noise mode to a higher frame rate mode.

In a particular example, the second mode may be selected when the imaging system is used for fluoroscopy or another application where a higher framerate may be desirable. Once an area of interest is identified, the first mode may be selected to generate an image with a lower noise, a lower dose, or the like. In another example, where binning is performed, such as 2×2, 3×3, 4×4, or greater binning, the pixel kTC noise may dominate over the data line related noise. The imaging system may be operated in the first mode to reduce the pixel kTC noise.

In some embodiments, a frame of data may not be available and/or may be discarded. For example, a first frame of data for frame N−1 may be used to generate the first values and other values. That frame of data may not be used to generate an image or a frame of a video signal. Instead, that data may be used to initialize the processing described above so that each subsequent frame may have available the values from the previous frame to perform the lower noise processing described above.

In some embodiments, the operations described above to reduce or eliminate pixel kTC noise may be applied to the imaging strip 104 described above. In particular, the imaging strip 104 may have a relatively shorter data line coupling the imaging strip 104 to the readout circuit 106-2. The common electronics 108 and the readout circuit 106-2 may be configured as described above to reduce kTC noise.

In some embodiments, the modes of operation described with respect to FIG. 14 may be switched depending on whether the imaging strip 104 is read. For example, if the imaging strip 104 is part of the imaging array 102, and the entire imaging array 102 is being read, the operations described above to reduce pixel kTC noise may not be performed. Because there are two measurements per data line, the background noise from the data lines is also measured twice. For imaging arrays 102 with longer data lines, this data line noise may dominate the pixel kTC noise.

Figure 15:
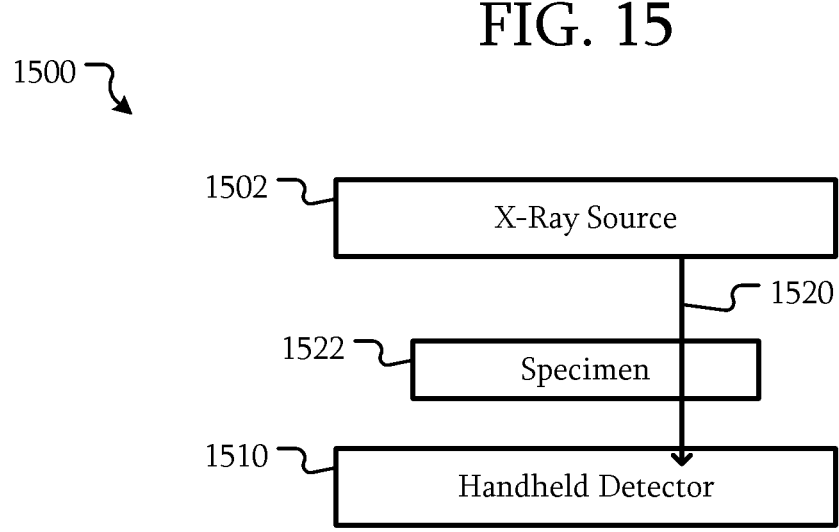
FIG. 15 is a block diagram of a 2D x-ray imaging system according to some embodiments.

FIG. 15 is a block diagram of a 2D x-ray imaging system according to some embodiments. The 2D x-ray imaging system 1500 includes an x-ray source 1502 and detector 1510. The detector 1510 may include an imaging system 100, 200, 400, 500, 600, 700a, 700b, 800a, 800b, 900, or the like as described above. The x-ray source 1502 is disposed relative to the detector 1510 such that x-rays 1520 may be generated to pass through a specimen 1522 and detected by the detector 1510. In some embodiments, the detector 1510 is part of a medical imaging system. In other embodiments, the 2D x-ray imaging system 1500 may include a portable vehicle scanning system as part of a cargo scanning system.

Some embodiments include a system, comprising: a housing 110; an imaging array 102 disposed within the housing 110; an imaging strip 104 disposed within the housing 110; a first readout circuit 106-1 coupled to the imaging array 102; a second readout circuit 106-2 coupled to the imaging strip 104; and common electronics 108 coupled to the first readout circuit 106-1 and the second readout circuit 106-2 and configured to generate image data in response to at least one of the first readout circuit 106-1 and the second readout circuit 106-2.

In some embodiments, the imaging array 102 and the imaging strip 104 are separate.

In some embodiments, the imaging array 102 and the imaging strip 104 are separate and formed on the same substrate 114.

In some embodiments, at least one of a size, layout, resolution, and internal components of pixels of the imaging array 102 is different from a corresponding at least one of a size, layout, resolution, and internal components of pixels of the imaging strip 104.

In some embodiments, the imaging strip 104 is a subset of the imaging array 102.

In some embodiments, the imaging strip 104 is less than 30% of the imaging array 102.

In some embodiments, the system further comprises data lines 618, 718, 818 coupled to the imaging array 102 and the imaging strip 104.

In some embodiments, the system further comprises a plurality of switches 722 dividing the data lines 718 into a plurality of first data lines 718b coupled to the imaging strip 104 and a plurality of second data lines 718b coupled to a remainder of the imaging array 102 outside of the imaging strip 104.

In some embodiments, the system further comprises a plurality of first data lines 618a coupled to the subset of the imaging array 102 including the imaging strip 104; a plurality of second data lines 618b separate from the first data lines 618a and coupled to the imaging array 102 outside of the imaging strip 104.

In some embodiments, the system further comprises an x-ray source configured to generate an x-ray beam; a detector disposed to receive the x-ray beam and including the housing 110, the imaging array 102, the imaging strip 104, the first readout circuit 106-1, the second readout circuit 106-2, and the common electronics 108.

Some embodiments include a method, comprising: reading first data from an imaging array 102 disposed within a housing 110 using at least a first readout circuit 106-1; reading second data from an imaging strip 104 disposed within the housing 110 using at least a second readout circuit 106-2; processing the first data in common electronics 108 to generate first image data; and processing the second data in the common electronics 108 to generate second image data.

In some embodiments, the imaging array 102 and the imaging strip 104 are separate.

In some embodiments, the imaging array 102 and the imaging strip 104 are formed on the same substrate 114.

In some embodiments, a pixel size of pixels of the imaging array 102 is different from a pixel size of pixels of the imaging strip 104.

In some embodiments, the imaging strip 104 is a subset of the imaging array 102.

In some embodiments, the imaging strip 104 is less than 30% of the imaging array 102.

In some embodiments, reading the first data from the imaging array 102 disposed within a housing 110 using at least the first readout circuit 106-1 comprises reading the first data from the imaging array 102 through first data lines 618, 718, 818; and reading the second data from the imaging strip 104 disposed within the housing 110 using at least the second readout circuit 106-2 comprises reading the second data from the imaging strip 104 using second data lines 618, 718, 818 different from the first data lines 618, 718, 818.

In some embodiments, reading the first data from the imaging array 102 disposed within a housing 110 using at least the first readout circuit 106-1 comprises reading the first data from the imaging array 102 through first data lines 618, 718, 818; and reading the second data from the imaging strip 104 disposed within the housing 110 using at least the second readout circuit 106-2 comprises reading the second data from the imaging strip 104 using second data lines 618, 718, 818; and further comprising electrically coupling the first data lines 618, 718, 818 to the second data lines 618, 718, 818 when reading the first data from the imaging array 102.

Some embodiments include a system, comprising: means for reading first data from an imaging array disposed within a housing; means for reading second data from an imaging strip disposed within the housing; means for processing the first data in common electronics 108 to generate first image data; and means for processing the second data in the common electronics 108 to generate second image data.

Examples of the means for reading first data from an imaging array disposed within a housing include the readout circuits 106-1 and associated data lines Examples of the means for reading second data from an imaging strip disposed within the housing include the readout circuits 106-2 and associated data lines.

Examples of the means for processing the first data in common electronics to generate first image data include the common electronics 108.

Examples of the means for processing the second data in the common electronics to generate second image data include the common electronics 108.

In some embodiments, the imaging strip 104 is a subset of the imaging array 102.

Some embodiments include a system, comprising: a plurality of pixels 902; a plurality of data lines 908 coupled to the pixels 902; a plurality of switches 906 coupling the pixels 902 to the data lines 908; a plurality of readout circuits 910-918 coupled to the data lines 908; control logic 903 coupled to the readout circuits 910-918, the control logic 903 configured to, for one of the pixels 902: acquire a first value for the pixel 902 while the corresponding switch 906 is in an off state; reset the corresponding readout circuit 910-918 corresponding for the pixel; acquire a second value for the pixel 902 after resetting the readout circuit; turn on the corresponding switch 906; acquire a third value for the pixel 902 after turning on the corresponding switch 906; and combine the first value, the second value, and the third value into a combined value for the pixel 902.

In some embodiments, the control logic 903 is further configured to, for the one of the pixels 902: store a stored value for the pixel 902 based on the first value; and combine the second value, the third value, and the stored value into the combined value for the pixel 902.

In some embodiments, the control logic 903 is further configured to, for the one of the pixels 902: before acquiring the first value for the pixel: reset the corresponding readout circuit; and acquire a fourth value for the pixel 902 while the corresponding switch 906 is in an on state; and combine the first value, the second value, the third value, and the fourth value into the combined value for the pixel 902.

In some embodiments, the control logic 903 is further configured to, for the one of the pixels 902: add the third value minus the second value and the first value minus the fourth value to combine the first value, the second value, the third value, and the fourth value into the combined value for the pixel 902.

In some embodiments, the control logic 903 is further configured to, for the one of the pixels 902: combine the first value and the fourth value into a first correlated value; combine the second value and the third value into a second correlated value; and combine the first correlated value and the second correlated value into the combined value for the pixel 902.

In some embodiments, the control logic 903 is further configured to, for the one of the pixels 902: acquire the first value for the pixel 902 for a subsequent frame without resetting the corresponding readout circuit.

In some embodiments, the control logic 903 is further configured to, for the one of the pixels 902: subtract the first value and the second value from the third value to combine the first value, the second value, and the third value into the combined value for the pixel 902.

In some embodiments, the control logic 903 is further configured to, for the one of the pixels 902: switch 906 between: a first mode of operation where the first value, the second value, and the third value are combined into the combined value for the pixel; and a second mode of operation where the second value, and the third value are combined into the combined value for the pixel 902 and acquiring the first value for the pixel 902 while the corresponding switch 906 is in the off state is not performed.

In some embodiments, the system further comprises an x-ray source configured to generate an x-ray beam; a detector including the pixels 902 and disposed to receive the x-ray beam.

Some embodiments include a method, comprising: acquiring a first value for a pixel 902 coupled to a data line through a switch 906 using a readout circuit 910-918 while the switch 906 is in an off state; resetting the readout circuit; acquiring a second value for the pixel 902 after resetting the readout circuit; turning on the switch 906; acquiring a third value for the pixel 902 after turning on the switch 906; and combining the first value, the second value, and the third value into a combined value for the pixel 902.

In some embodiments, the method further comprises storing a stored value for the pixel 902 based on the first value; and wherein combining the first value, the second value, and the third value into the combined value for the pixel 902 comprises combining the second value, the third value, and the stored value into the combined value for the pixel 902.

In some embodiments, the method further comprises before acquiring the first value for the pixel: resetting the readout circuit; and acquiring a fourth value for the pixel 902 while the switch 906 is in an on state; and wherein combining the first value, the second value, and the third value into the combined value for the pixel 902 comprises combining the first value, the second value, the third value, and the fourth value into the combined value for the pixel 902.

In some embodiments, combining the first value, the second value, the third value, and the fourth value into the combined value for the pixel 902 comprises: adding the third value minus the second value and the first value minus the fourth value.

In some embodiments, the method further comprises combining the first value and the fourth value into a first correlated value; combining the second value and the third value into a second correlated value; and combine the first correlated value and the second correlated value into the combined value for the pixel 902.

In some embodiments, the method further comprises acquiring the first value for the pixel 902 for a subsequent frame without resetting the corresponding readout circuit.

In some embodiments, combining the first value, the second value, and the third value into the combined value for the pixel 902 comprises: subtracting the first value and the second value from the third value.

In some embodiments, the method further comprises switching between: a first mode of operation where the first value, the second value, and the third value are combined into the combined value for the pixel; and a second mode of operation where the second value, and the third value are combined into the combined value for the pixel 902 and acquiring the first value for the pixel 902 while the corresponding switch 906 is in the off state is not performed.

In some embodiments, the method further comprises generating an x-ray beam using an x-ray source; and generating an image using a detector including the pixel 902 disposed to receive the x-ray beam.

Some embodiments include a system, comprising: means for acquiring a first value for a pixel coupled to a data line through a switch using a readout circuit while the switch is in an off state; means for resetting the readout circuit; means for acquiring a second value for the pixel after resetting the readout circuit; means for turning on the switch; means for acquiring a third value for the pixel after turning on the switch; and means for combining the first value, the second value, and the third value into a combined value for the pixel.

Examples of the means for acquiring a first value for a pixel coupled to a data line through a switch using a readout circuit while the switch is in an off state include the switches 906, row drivers 901, data lines 908, and readout circuits 910-918.

Examples of the means for resetting the readout circuit include the switch 910a and control logic 903.

Examples of the means for acquiring a second value for the pixel after resetting the readout circuit include the switches 906, row drivers 901, data lines 908, and readout circuits 910-918

Examples of the means for turning on the switch include the control logic 903.

Examples of the means for acquiring a third value for the pixel after turning on the switch include the switches 906, row drivers 901, data lines 908, and readout circuits 910-918.

Examples of the means for combining the first value, the second value, and the third value into a combined value for the pixel include the switches 906, row drivers 901, data lines 908, readout circuits 910-918, and the external computer 913.

In some embodiments, the system further comprises means for acquiring the first value for the pixel for a subsequent frame without resetting the corresponding readout circuit. Examples of the means for acquiring the first value for the pixel for a subsequent frame without resetting the corresponding readout circuit include the switches 906, row drivers 901, data lines 908, and readout circuits 910-918.

Although particular examples of means for performing particular functions have been described above, in other embodiments, the particular functions may be performed by other means described herein.

Although the structures, devices, methods, and systems have been described in accordance with particular embodiments, one of ordinary skill in the art will readily recognize that many variations to the particular embodiments are possible, and any variations should therefore be considered to be within the spirit and scope disclosed herein. Accordingly, many modifications may be made by one of ordinary skill in the art without departing from the spirit and scope of the appended claims.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the claims beginning with claim [x] and ending with the claim that immediately precedes this one," where the bracketed term "[x]" is replaced with the number of the most recently recited independent claim. For example, for the first claim set that begins with independent claim 1, claim 4 can depend from either of claims 1 and 3, with these separate dependencies yielding two distinct embodiments; claim 5 can depend from any one of claim 1, 3, or 4, with these separate dependencies yielding three distinct embodiments;

claim 6 can depend from any one of claim 1, 3, 4, or 5, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed to cover the corresponding structure, material, or acts described herein and equivalents thereof in accordance with 35 U.S.C. § 112(f). Embodiments of the invention in which an exclusive property or privilege is claimed are defined as follows.

The invention claimed is:

1. A system, comprising:
a plurality of pixels;
a plurality of data lines;
a plurality of switches coupling the pixels to the data lines, wherein each of the pixels is coupled to a corresponding one of the data lines through a corresponding one of the switches;
a plurality of readout circuits coupled to the data lines, wherein each of the data lines is coupled to a corresponding one of the readout circuits;
control logic coupled to the readout circuits, the control logic configured to, for one of the pixels:
acquire a first value for the pixel while the corresponding switch is an off state;
reset the corresponding readout circuit;
acquire a second value for the pixel after resetting the readout circuit;
turn on the corresponding switch;
acquire a third value for the pixel after turning on the corresponding switch; and
combine the first value, the second value, and the third value into a combined value for the pixel.

2. The system of claim 1, wherein the control logic is further configured to, for the one of the pixels:
store a stored value for the pixel based on the first value; and
combine the second value, the third value, and the stored value into the combined value for the pixel.

3. The system of claim 1, wherein the control logic is further configured to, for the one of the pixels:
before acquiring the first value for the pixel:
reset the corresponding readout circuit; and
acquire a fourth value for the pixel while the corresponding switch is in an on state; and
combine the first value, the second value, the third value, and the fourth value into the combined value for the pixel.

4. The system of claim 3, wherein the control logic is further configured to, for the one of the pixels:
add the third value minus the second value and the first value minus the fourth value to combine the first value, the second value, the third value, and the fourth value into the combined value for the pixel.

5. The system of claim 3, wherein the control logic is further configured to, for the one of the pixels:
combine the first value and the fourth value into a first correlated value;
combine the second value and the third value into a second correlated value; and
combine the first correlated value and the second correlated value into the combined value for the pixel.

6. The system of claim 1, wherein the control logic is further configured to, for the one of the pixels:
acquire the first value for the pixel for a subsequent frame without resetting the corresponding readout circuit.

7. The system of claim 1, wherein the control logic is further configured to, for the one of the pixels:
subtract the first value and the second value from the third value to combine the first value, the second value, and the third value into the combined value for the pixel.

8. The system of claim 1, wherein the control logic is further configured to, for the one of the pixels:
switch between:
a first mode of operation where the first value, the second value, and the third value are combined into the combined value for the pixel; and
a second mode of operation where the second value, and the third value are combined into the combined value for the pixel and acquiring the first value for the pixel while the corresponding switch is in the off state is not performed.

9. The system of claim 1, further comprising:
an x-ray source configured to generate an x-ray beam;
a detector including the pixels and disposed to receive the x-ray beam.

10. A method, comprising:
acquiring a first value for a pixel coupled to a data line through a switch using a readout circuit while the switch is in an off state;
resetting the readout circuit;
acquiring a second value for the pixel after resetting the readout circuit;
turning on the switch;
acquiring a third value for the pixel after turning on the switch; and
combining the first value, the second value, and the third value into a combined value for the pixel.

11. The method of claim 10, further comprising:
storing a stored value for the pixel based on the first value; and
wherein combining the first value, the second value, and the third value into the combined value for the pixel comprises combining the second value, the third value, and the stored value into the combined value for the pixel.

12. The method of claim 10, further comprising:
before acquiring the first value for the pixel:
resetting the readout circuit; and
acquiring a fourth value for the pixel while the switch is in an on state; and
wherein combining the first value, the second value, and the third value into the combined value for the pixel comprises combining the first value, the second value, the third value, and the fourth value into the combined value for the pixel.

13. The method of claim 12, wherein combining the first value, the second value, the third value, and the fourth value into the combined value for the pixel comprises:
adding the third value minus the second value and the first value minus the fourth value.

14. The method of claim 12, further comprising:
combining the first value and the fourth value into a first correlated value;
combining the second value and the third value into a second correlated value; and
combine the first correlated value and the second correlated value into the combined value for the pixel.

15. The method of claim 10, further comprising:
acquiring the first value for the pixel for a subsequent frame without resetting the corresponding readout circuit.

16. The method of claim 10, wherein combining the first value, the second value, and the third value into the combined value for the pixel comprises:
subtracting the first value and the second value from the third value.

17. The method of claim 10, further comprising switching between:
- a first mode of operation where the first value, the second value, and the third value are combined into the combined value for the pixel; and
- a second mode of operation where the second value, and the third value are combined into the combined value for the pixel and acquiring the first value for the pixel while the corresponding switch is in the off state is not performed.

18. The method of claim 10, further comprising:
generating an x-ray beam using an x-ray source; and
generating an image using a detector including the pixel disposed to receive the x-ray beam.

19. A system, comprising:
means for acquiring a first value for a pixel coupled to a data line through a switch using a readout circuit while the switch is in an off state;
means for resetting the readout circuit;
means for acquiring a second value for the pixel after resetting the readout circuit;
means for turning on the switch;
means for acquiring a third value for the pixel after turning on the switch; and
means for combining the first value, the second value, and the third value into a combined value for the pixel.

20. The system of claim 19, further comprising:
means for acquiring the first value for the pixel for a subsequent frame without resetting the corresponding readout circuit.

* * * * *